United States Patent [19]

Kami et al.

[11] Patent Number: 5,107,844
[45] Date of Patent: Apr. 28, 1992

[54] ULTRASONIC OBSERVING APPARATUS

[75] Inventors: Kuniaki Kami; Takahiro Echizenya; Kazuhiro Misono, all of Hachioji, Japan

[73] Assignee: Olympus Optical Co., Ltd., Tokyo, Japan

[21] Appl. No.: 473,548

[22] Filed: Feb. 1, 1990

[30] Foreign Application Priority Data

| Apr. 6, 1989 [JP] | Japan | 1-87259 |
| Apr. 7, 1989 [JP] | Japan | 1-86943 |
| Apr. 13, 1989 [JP] | Japan | 1-96093 |

[51] Int. Cl.$^5$ ............................................. A61B 8/12
[52] U.S. Cl. ............................. 128/662.06; 128/660.1
[58] Field of Search ............... 128/660.08–660.10, 128/662.06, 916; 73/633

[56] References Cited

U.S. PATENT DOCUMENTS

| 4,271,706 | 6/1981 | Ledley | 128/916 |
| 4,543,960 | 10/1985 | Harui et al. | 128/662.06 |
| 4,722,345 | 2/1988 | Ueno et al. | 128/660.09 |
| 4,817,616 | 4/1989 | Goldstein | 128/662.06 |
| 4,917,096 | 4/1990 | Englehart et al. | 73/633 |

FOREIGN PATENT DOCUMENTS

| 0253268 | 1/1988 | European Pat. Off. |
| 56-143148 | 11/1981 | Japan |
| 57-9439 | 1/1982 | Japan |
| 60-5134 | 1/1985 | Japan |
| 63-74108 | 5/1988 | Japan |

*Primary Examiner*—Francis Jaworski
*Attorney, Agent, or Firm*—Armstrong & Kubovcik

[57] ABSTRACT

An ultrasonic observing apparatus includes an ultrasonic wave transmitting and receiving apparatus for transmitting and receiving ultrasonic waves, a first scanning apparatus for moving the direction in which the ultrasonic wave transmitting and receiving apparatus transmits and receives waves so that a first ultrasonic tomographic image may be obtained, a second scanning apparatus for moving the direction in which the ultrasonic wave transmitting and receiving apparatus transmits and receives waves so that a second ultrasonic tomographic image intersecting with the first ultrasonic tomographic image may be obtained and a control apparatus for controlling the first scanning apparatus and second scanning apparatus as related with each other.

26 Claims, 28 Drawing Sheets

SIGNAL TRANSMITTING PULSE

ECHO IN THE CASE OF LOW FREQUENCY

ECHO IN THE CASE OF HIGH FREQUENCY

SIGNAL TRANSMITTING PULSE

ECHO

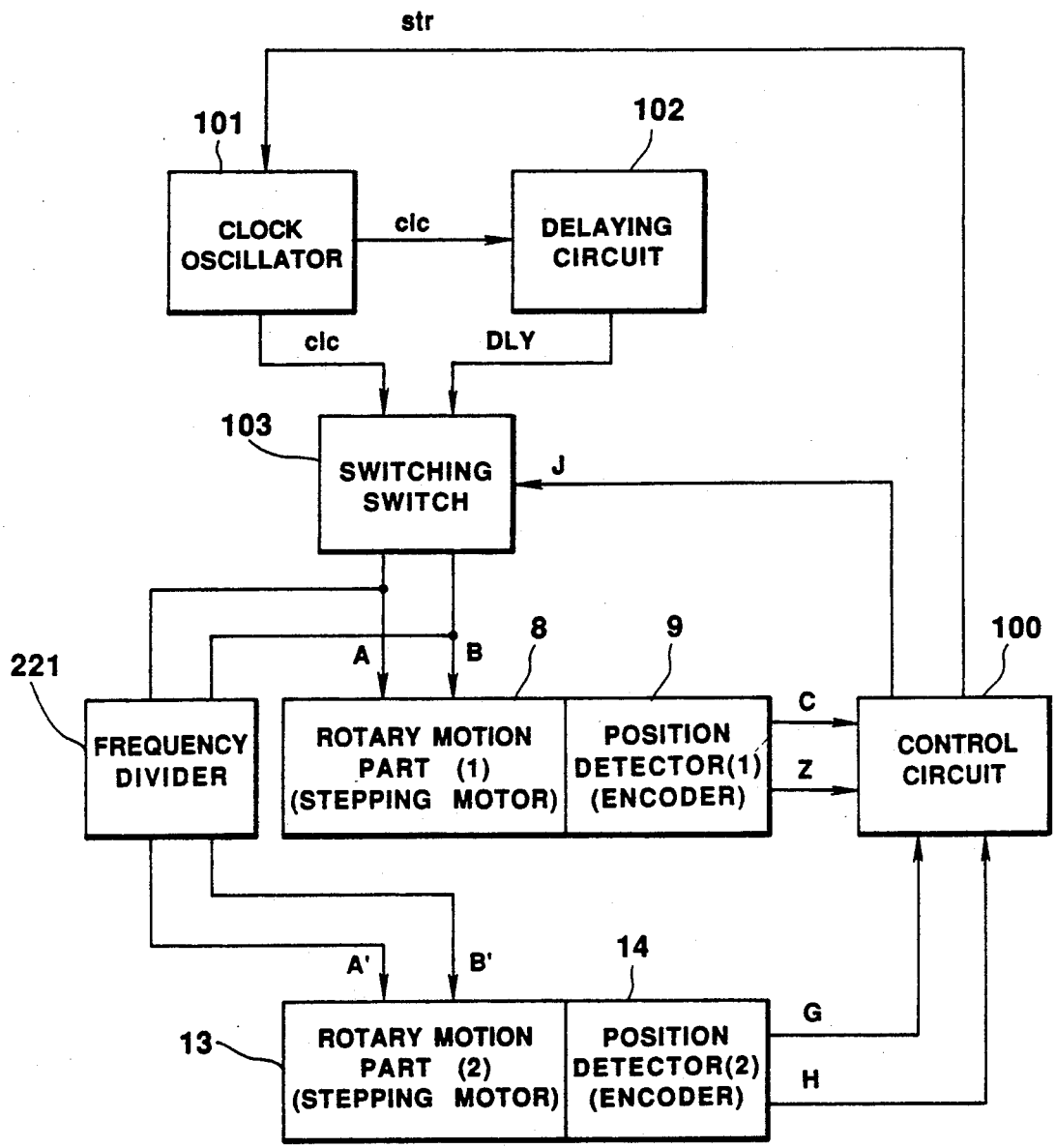
FIG. 10
FIG.11 (a) A 
FIG.11 (b) A' 

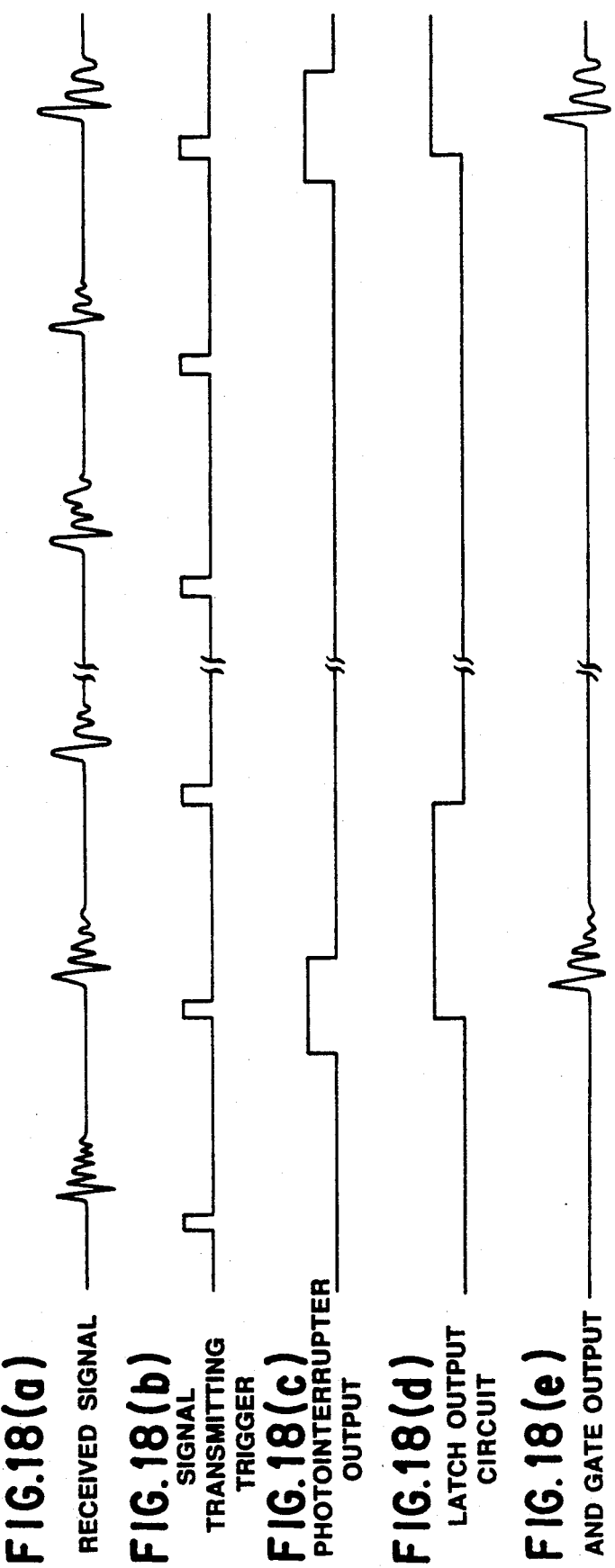

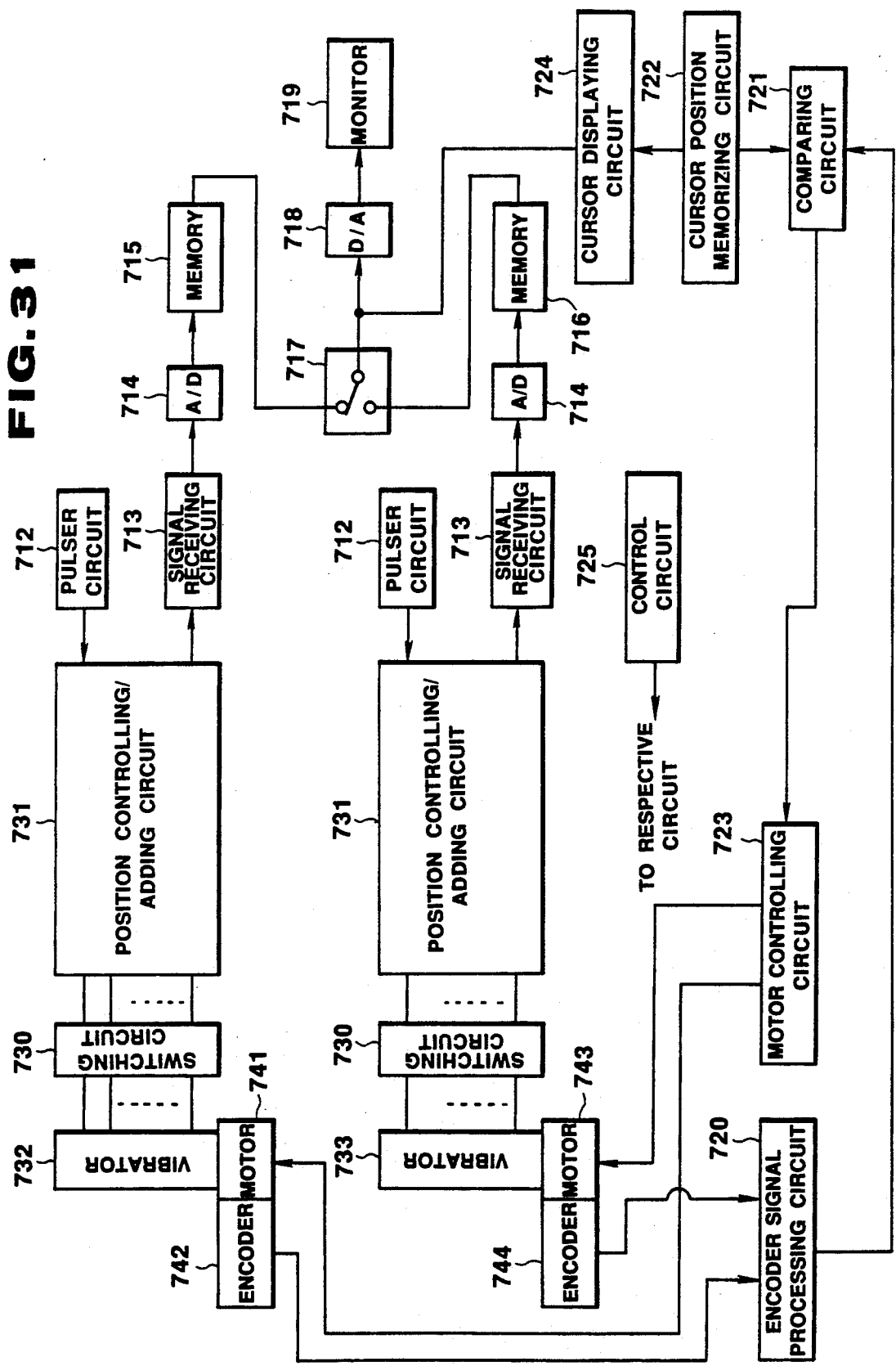

RELATED ART RELATED ART

ULTRASONIC OBSERVING APPARATUS

BACKGROUND OF THE INVENTION

1. Field of the Invention:

This invention relates to an ultrasonic observing apparatus for obtaining a tomographic image of an inspected object by an ultrasonic pulse echo method.

2. Related Art Statement:

There is already an ultrasonic probe for obtaining a tomographic image of a body interior from within a body cavity. The conventional ultrasonic probe has been mostly for a display purpose by a single scanning system such as linear scanning, radial scanning or sector scanning system.

However, when observing plaque or the like within a vein, it has been desired to three-dimensionally catch an image by simultaneously displaying a linear image and a radial image.

Therefore, so far a process such as is shown in FIG. 32(A) has been used wherein an ultrasonic probe 401 having an ultrasonic vibrator on one side is rotated by one round to be advanced and retreated to take several tomographic images which are processed to display linear images and radial images. In such a case, as shown, for example, in FIG. 33(A), the radial planes 1 to 8 are taken in by one scanning, only a fourth radial image such as the left side image of the displayed images shown in FIG. 33(B) is displayed, one scanning line in the radial planes 1 to 8 is sequentially taken in and such linear images as the right side images of the displayed image shown in FIG. 33(B) are displayed. By repeating such operations, radial images and linear images are displayed in one picture.

As such a apparatus whereby radial images and linear images can be obtained, an apparatus wherein an ultrasonic probe can make a radial scanning and can be moved in the axial direction is disclosed in the publication, for example, of Japanese Patent Application Laid Open No. 9439/1982 or Japanese Utility Model Application Laid Open No. 74108/1988. Also, an apparatus wherein an electronic scanning vibrator is made rotatable is disclosed in U.S. Pat. No. 4,543,960 and an apparatus wherein a vibrator is made rotatable for two axes is disclosed in EPC Patent Laid Open No. 0253268.

Also, as a scanning system for simultaneously displaying a radial image and a linear image, there is considered a spiral system wherein, as shown in FIG. 34, a probe 401 is advanced and retreated at any time and a probe is rotated with it. In such a case, there will be no problem with regard to the linear image but the scanning line of one radial image picture will be in the range x shown in FIG. 34(A) and the starting point and ending point will be different from each other. However, if the advancing and retreating speed is significantly lower than the rotating speed, there will be substantially no difference of the starting point and ending point and there will be no problem.

In such a scanning system as in FIG. 32(A) wherein radial images are taken in one by one as in the past, unless the probe 401 tip is positioned, that is, the starting point and ending point are accurately determined, the linear image will become low in resolution. The probe tip is desired to be stopped with the vibrating surface just above as, for example, in FIG. 32(B) but will be directed in an oblique direction by the inertia force as in FIG. 32(C). Then, in the case of displaying a linear image, the direction resolution will not be determined only by the ultrasonic vibrator 402 of the probe 401 but will depend on the positioning of the ultrasonic vibrator 402 and the resolution will deteriorate.

Also, as shown in FIGS. 34(a)-34(c), in the case of making a spiral scanning, as the rotary motor and advancing and retreating motor are independent of each other, they must be controlled in speed respectively individually. Then, in case the spiral scanning in FIG. 34(A) is made a reference, when the advancing and retreating speed against the rotation speed is increased to be higher than in the reference, it will be as in FIG. 34(B) but, when the advancing and retreating speed is reduced, it will be as in FIG. 34(C). Then, there will be disadvantages that the displaying surface will vary in the scanning position for a radial image will vary in the scanning range (resolution) for a linear image.

As characterisics of ultrasonic waves, the lower the frequency, the farther they will travel while the higher the frequency, the sooner the waves will be attenuated and the less distance they travel. Therefore, when the attenuation of ultrasonic waves is considered, in case an ultrasonic wave of a low frequency is used, it will be necessary to see it a long distance and the scanning speed had better be low. On the other hand, in case an ultrasonic wave of a high frequency is used, the scanning speed will be able to be increased. Therefore, in case the frequency of the ultrasonic wave is varied by replacing the ultrasonic vibrator 402, in order to obtain the optimum frame rate, it will be necessary to make the scanning speed corresponding to that frequency.

A technique of synchronizing the transmission of an ultrasonic wave and the rotation of an ultrasonic vibrator with each other is disclosed in the publication of Japanese Patent Application Laid Open No. 5134/1985. However, even if this technique is used, as the rotation and the advance or retreat of the ultrasonic vibrator are controlled independently of each other, the above described disadvantages will not be solved.

Also, in the conventional ultrasonic diagnosis, it is difficult to locate an affected part with one tomographic image. Therefore, particularly, in a single scanning type diagnosing apparatus, the diagnosis has been made by moving the position of an ultrasonic probe. In such a case, the ultrasonic probe has been manually moved, has been therefore difficult to position and has been likely to miss an affected part.

Further, moving the ultrasonic probe will give a pain to the examinee.

Also, in the apparatus shown in the publications of the above mentioned Japanese Patent Application Laid Open No. 9439/1982 and Japanese Utility Model Application No. 74108/1988, in order to obtain a linear scanned image, the rotary motion must be stopped, the rotary motion and advancing and retreating motion switching mechanism and positioning mechanism are required, the formation is complicated and the tomographic image of the desired part to be observed can not be quickly obtained.

There is also a method wherein data is stored in a memory and an image of any cross-section is obtained from the data in the memory. However, in such a case, many memories will be required and the circuit formation will be complicated.

Another apparatus, wherein one tomographic image of an inspected object and the other tomographic image intersecting with this tomographic image are displayed while showing the position relation of both so that various disease nests may be recognized as three-dimensional images, is disclosed in the publication of Japanese Patent Application Laid Open No. 143148/1981. This is to make three-dimensional a tomographic image by combining an electronic linear scanning and electronic sector scanning with each other.

However, in this apparatus, there are disadvantages that, in case it is necessary to change the positional relationship of the two tomographic images in order to obtain an objective tomographic image, the operator will have to manually operate them on the hand base side and a tomographic image of a desired part to be observed will not be able to be quickly obtained. Also, in the above mentioned apparatus, there is a disadvantage that, though the part in which the two tomographic images intersect with each other can be shown, the two tomographic images can not be made to intersect with each other to be displayed by automatically moving the scanning position to the desired part to be observed.

In such apparatus wherein both of a mechanical linear scanning and mechanical radial scanning can be worked as is disclosed in the above mentioned Japanese Utility Model Application Laid Open No. 7410/1988, there is a method wherein the mechanical linear scanning and mechanical radial scanning are simultaneously made, three-dimensional data is taken in and is stored in a memory as described above and an image of any cross-section is obtained from the data in the memory. However, there are disadvantages that, in such a case, it will take time to display the two tomographic images and also to select tomographic image to be observed.

Objects and Summary of the Invention:

An object of the present invention is to provide an ultrasonic observing apparatus wherein, even if the scanning speed is changed, a tomographic image by a plurality of such scanning systems as radial scanning and linear scanning systems can be always obtained under fixed conditions in relation to each other.

Another object of the present invention is to provide an ultrasonic observing apparatus wherein, with a simple formation, while scans by a plurality of scanning systems are being simultaneously made, a tomographic image of any position can be obtained.

Further another object of the present invention is to provide an ultrasonic observing apparatus wherein a tomographic image by a plurality of scanning systems is obtained and a tomographic image by the other scanning system in a designated position on a tomographic image by one scanning system can be obtained.

An ultrasonic observing apparatus according to the present invention comprises an ultrasonic wave transmitting and receiving device for transmitting and receiving ultrasonic waves, a first scanning device for moving the direction in which the above mentioned ultrasonic wave transmitting and receiving device transmits and receives waves so that a first ultrasonic tomographic image may be obtained, a second scanning device for moving the direction in which the above mentioned ultrasonic wave transmitting and receiving device transmits and receives waves so that a second ultrasonic tomographic image intersecting with the above mentioned first ultrasonic tomographic image may be obtained and a control device for controlling the above mentioned first scanning device and second scanning device as related with each other.

The other features and advantages of the present invention will become apparent enough with the following explanation.

BRIEF DESCRIPTION OF THE DRAWINGS

FIGS. 1 to 7 relate to the first embodiment of the present invention.

FIG. 1 is a block diagram showing an ultrasonic probe controlling system.

FIG. 2 is a sectioned view showing the formation of a signal processing system of an ultrasonic observing apparatus including an ultrasonic probe driving part and ultrasonic probe.

FIGS. 3(a)-3(h) are a timing charts for explaining the operation of this embodiment.

FIG. 4 is a circuit diagram showing JK - FF producing a control signal inverting the scanning direction.

FIG. 5 is a block diagram showing the formation of a clock oscillator.

FIG. 6 is a circuit diagram showing the formation of a delaying circuit.

FIGS. 10 and 11 relate to the fourth embodiment of the present invention.

FIG. 10 is a block diagram showing an ultrasonic probe controlling system.

FIGS. 11(a)-11(b) are timing charts showing a stepping motor driving signal.

FIGS. 13 to 20 relate to the sixth embodiment of the present invention.

FIG. 13 is a block diagram showing the formation of a control system of an ultrasonic observing apparatus.

FIG. 14 is a sectioned view showing the formation of an ultrasonic observing apparatus driving system.

FIG. 15 is an explanatory view showing the scanning of an ultrasonic probe.

FIG. 16 is a block diagram showing the formation of a signal extracting circuit.

FIG. 17 is an explanatory view showing a cross-section by a signal extracted in the signal extracting circuit.

FIGS. 18(a)-18(e) are waveform diagrams for explaining the operation of the signal extracting circuit.

FIG. 19 is a perspective view showing the formation of a linearly scanned cross-section position designating means.

FIG. 20 is an explanatory view showing the formation of a radially scanned cross-section position designating means.

FIGS. 23 to 26 relate to the ninth embodiment of the present invention.

FIG. 23 is a sectioned view of an essential part showing the formation of an ultrasonic observing apparatus driving system.

FIG. 24 is a block diagram showing the formation of a signal processing system of the ultrasonic observing apparatus.

FIG. 25 is a perspective view of the entire ultrasonic observing apparatus.

FIGS. 27 and 28 relate to the tenth embodiment of the present invention.

FIG. 28 is a block diagram showing the formation of a signal processing system of the ultrasonic observing apparatus.

FIG. 29(A) is a sectioned view of an essential part showing the formation of an ultrasonic observing apparatus driving system.

FIG. 29(B) is an elevation of an ultrasonic vibrator.

FIGS. 30 and 31 relate to the 12th embodiment of the present invention.

FIG. 30 is a perspective view of an ultrasonic probe.

FIG. 31 is a block diagram showing the formation of a signal processing system of an ultrasonic observing apparatus.

DETAILED DESCRIPTION OF THE PREFERRED EMBODIMENTS

In FIGS. 1 to 7 is shown the first embodiment of the present invention.

Figure 2:
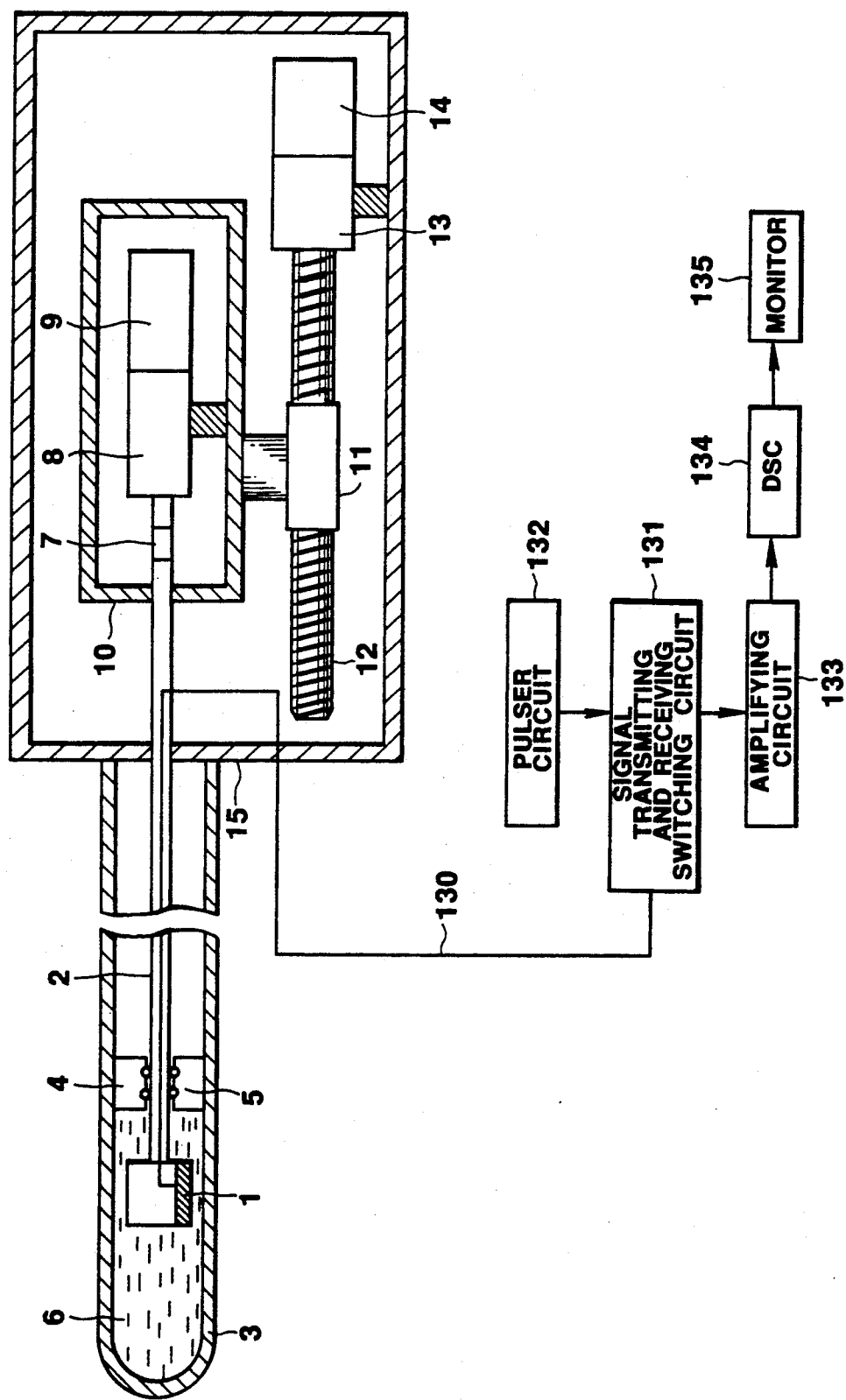
Figure 3:
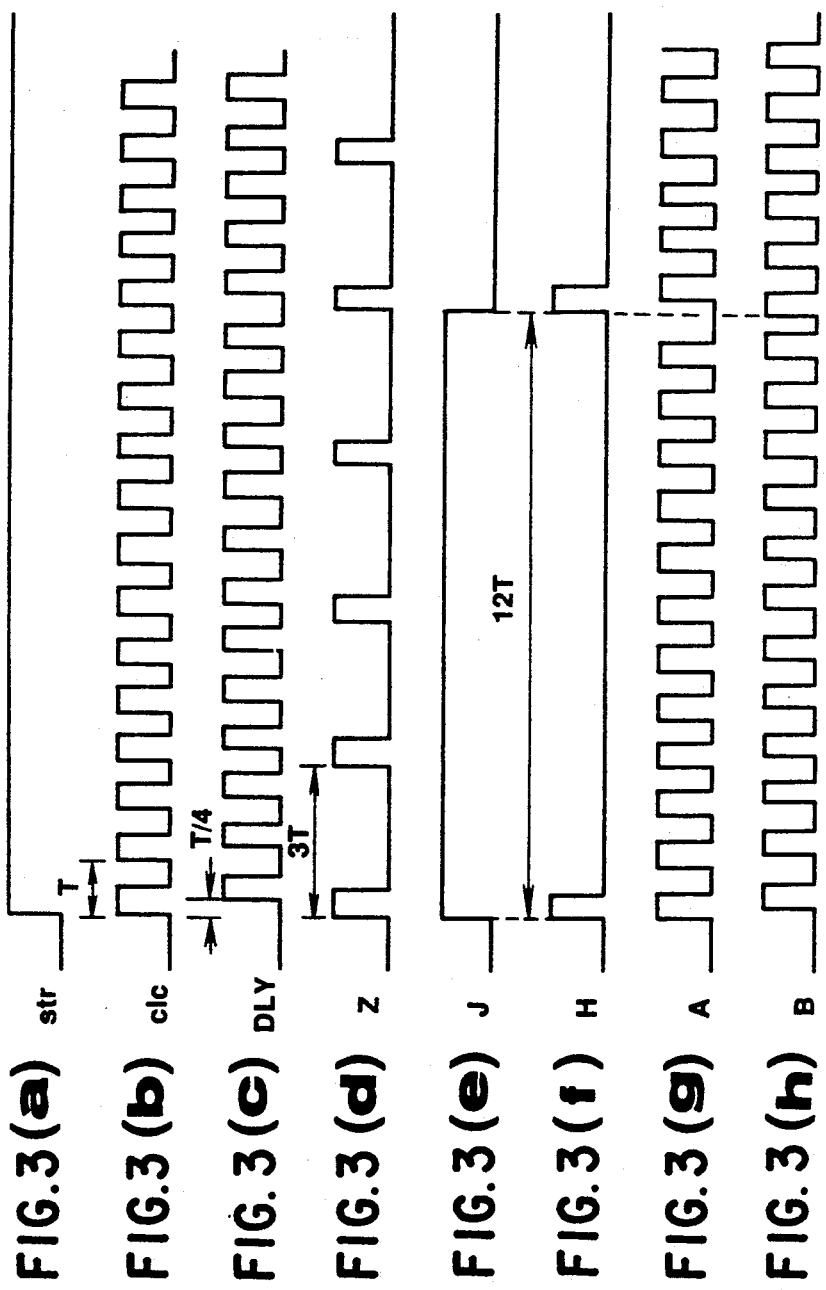

First of all, with reference to FIG. 2, the formation of a signal processing system of an ultrasonic observing apparatus including an ultrasonic probe driving system and ultrasonic probe of this embodiment shall be explained.

An ultrasonic vibrator 1 to be an ultrasonic wave transmitting and receiving part is connected to a shaft-like drive transmitting part 2 and these are contained in an outer tube 3 spherically closed at the tip. A sealing member 4 and O-rings 5 are provided on the tip side within the above mentioned outer tube 3 so as to hold the above mentioned drive transmitting part 2. The space within the tip part of the outer tube 3 sealed by the above mentioned outer tube 3, sealing member 4 and O-rings 5 is filled with an acoustic medium 6. The above mentioned drive transmitting part 2 and outer tube 3 may be made flexible.

The above mentioned drive transmitting part 2 is extended at the rear end out of the above mentioned outer tube 3 at the rear end and is connected through a connecting part 7 to a rotary motion part (1) 8 consisting of a stepping motor. This rotary motion part (1) 8 is formed as combined with a position detector (1) 9 consisting of an encoder detecting the rotating position of this rotary motion part (1) 8. These are contained and held within a rotary motion part outer fitting 10.

The above mentioned rotary motion part outer fitting 10 is fitted to an advancing and retreating motion transmitting part 11 which is screwed with an advancing and retreating mechanism part 12 consisting of a ball screw. The above mentioned advancing and retreating mechanism part 12 is connected to the rotary motion part (2) 13 driving part so as to be rotated by this rotary motion part (2) 13. The above mentioned rotary motion part (2) 13 is formed as combined with a position detector (2) 14 consisting of an encoder detecting the rotating position of this rotary motion part (2) 13.

The above mentioned connecting part 7, rotary motion part (1) 8, position detector (1) 9, rotary motion part outer fitting 10, advancing and retreating motion transmitting part 11, advancing and retreating mechanism part 12, rotary motion part (2) 13 and position detector (2) 14 are enclosed with an outer fitting 15 to which the above mentioned outer tube 3 is fixed at the rear end and the above mentioned rotary motion part (2) 13 is also fixed.

Also, the above mentioned ultrasonic vibrator 1 is connected through a cable 130 to a signal transmitting and receiving switching circuit 131 within an observing apparatus not illustrated. This signal transmitting and receiving switching circuit 131 is connected to a pulser circuit 132 generating a signal transmitting pulse and an amplifying circuit 133 amplifying a received signal. The signal transmitting pulse from the pulser circuit 132 is transmitted to the ultrasonic vibrator 1 through the signal transmitting and receiving switching circuit 131 so that an ultrasonic wave may be emitted from this ultrasonic vibrator 1 toward an object to be inspected. The echo from the object is received by the ultrasonic vibrator 1 and is input into the amplifying circuit 133 through the signal transmitting and receiving switching circuit 131. The output of this amplifying circuit 133 is input into a DSC (digital scan converter) 134. The output of the above mentioned DSC 134 is input into a monitor 135 on which an ultrasonic tomographic image will be displayed.

Figure 1:
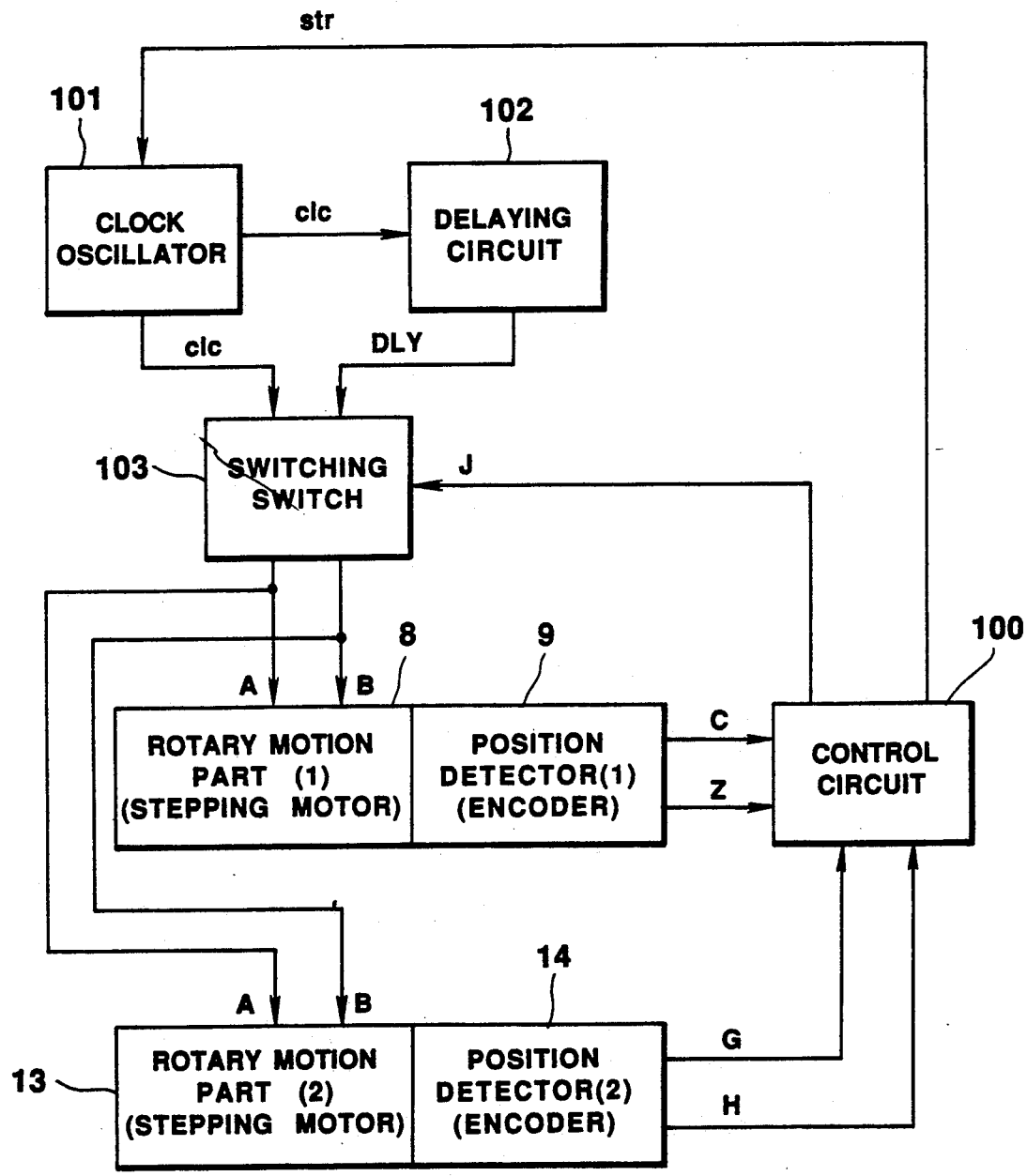

With reference to FIG. 1, the formation of an ultrasonic probe controlling system shall be explained.

The ultrasonic probe comprises a control circuit 100 controlling the rotation, advance and retreat of the vibrator 1, a clock oscillator 101 inputting a starting signal str from this control circuit 100 and outputting a clock clc and a delaying circuit 102 inputting the clock clc from the above mentioned clock oscillator 101 and outputting a signal DLY delayed by ¼ of a period T from this clock clc. The above mentioned clock clc and signal DLY are input a driving signals of two phases respectively into the stepping motor which is the rotary motion part (1) 8 and the stepping motor which is the rotary motion part (2) 13 through a switching switch 103. The above mentioned switching switch 103 is controlled by a control signal J from the above mentioned control circuit 100 so as to switch the state that the clock clc is of an A phase and the signal DLY is of a B phase and the state that the clock clc is of a B phase and the signal DLY is of an A phase to each other.

The A phase output C of the encoder which is the position detector (1) 9 connected to the above mentioned rotary motion part (1) 8 and the Z phase output Z output per rotation are input into the above mentioned control circuit 100. In the same manner, the A phase output G and Z phase output H of the encoder which is the position detector (2) 14 connected to the above mentioned rotary motion part (2) 13 are input into the above mentioned control circuit 100.

The operation of this embodiment shall be explained in the following.

First of all, by the control circuit 100, a starting signal str is made High and is input into the clock oscillator 101 which will output a clock clc when the above mentioned signal str becomes High. This clock clc is input into the delaying circuit 102 which outputs a signal DLY delayed by ¼ T of the frequency T of the clock clc. The above mentioned clock clc and signal DLY are input respectively as driving signals of the A phase and B phase into the stepping motor which is the rotary motion part (1) 8 and the stepping motor which is the rotary motion part (2) 13 through the switching switch 103 controlled by a control signal J from the control circuit 100. By this driving signal, both stepping motors are rotated.

The stepping motor of the rotary motion part (1) 8 rotates the vibrator 1 through the connecting part 7 and drive transmitting part 2. Also, the stepping motor of the rotary motion part (2) 13 rotates the ball screw which is the advancing and retreating mechanism part 12. Then, the advancing and retreating motion transmitting part 11 connected to this ball screw makes an advancing and retreating motion. Then, the rotary motion part outer fitting 10 connected to the advancing and retreating motion transmitting part also makes an advancing and retreating motion by which the vibrator 1 is advanced and retreated through the drive transmitting part 2.

The rotating position of the above mentioned rotary motion part (1) 8 is read out by the encoder which is the position detector (1) 9 and the A phase output C and Z phase output Z of this encoder are input into the above mentioned control circuit 100. The rotating position of the rotary motion part (2) 13 is read out by the encoder which is the position detector (2) 14 and the A phase output G and Z phase output H of this encoder are input into the above mentioned control circuit 100. This control circuit 100 produces a control signal J, for example, based on the above mentioned Z phase output H so that the the switching switch 103 may be thereby switched.

An example of an actual timing shall be explained by using FIGS. 3(a)–3(h).

In this example, a radial 1 frame is of six scans and a linear 1 frame is of 24 scans. In fact, the radial 1 frame is of a level of 512 scans and the linear 1 frame is of a level of about 128 scans.

First of all, when a starting signal str from the control circuit 100 becomes High as shown in FIG. 3(a), a clock clc will be oscillated by the oscillator 101 as shown in FIG. 3(b). At the same time, the clock clc will be delayed by ¼ T by the delaying circuit 102 and such signal DLY as is shown in FIG. 3(c) will be output.

The above mentioned clock clc and signal DLY are input into the rotary motion part (1) 8 and rotary motion part (2) 13 through the switching switch 103. In these rotary motion part (1) 8 and rotary motion part (2) 13, by such two input phases of the A phase and B phase as are shown in FIGS. 3(g) and (h). a normal rotation and reverse rotation are determined. In this embodiment, at the time when the B phase rises, if the signal of the A phase is High, the rotation will be normal but, if the signal is Low, the rotation will be reverse. Also, in this embodiment, the A phase or B phase from the switching switch 103 is input into the pulser circuit 132 and ultrasonic waves are output from the vibrator 1 at the edge of the pulse of this A phase or B phase. Therefore, as shown in FIG. 3(d), from the position detector (1) 9, the Z phase Z will be output every 3T and, as shown in FIG. 3(f), from the position detector (2) 14, the Z phase H will be output every 12T.

Therefore, in the radial 1 frame 6 scans, if 4 frames are taken, 1 scan will end. Until this 1 scan ends, by the phase difference of the A and B signals, the rotary motion part (1) 8 and rotary motion part (2) 13 will both continue to rotate normally. Thereby, the vibrator 1 will make a retreating motion while normally rotating and will continue the same motion until one scan ends.

When the Z phase outut H is output from the position detector (2) 14, this signal will be input into the control circuit 100 and a control signal J as is shown in FIG. 3(e) will be transmitted to the switching switch 103. Then, as shown in FIGS. 3(g) and (h), the phases of the A and B signals will be switched and the rotary motion part (1) 8 and rotary motion part (2) 13 will both rotate reversely. Thereby, the vibrator 1 will make an advancing motion while reversely rotating and will continue the same motion until one scan ends. When this one scan ends, the vibrator 1 will resume a retreating motion while again rotating normally.

The above mentioned rotary motion part (1) 8 and rotary motion part (2) 13 are both driven by the same driving signals A and B and are therefore synchronized and the rotary motion and advancing and retreating motion of the vibrator 1 are synchronized with each other.

Figure 4:
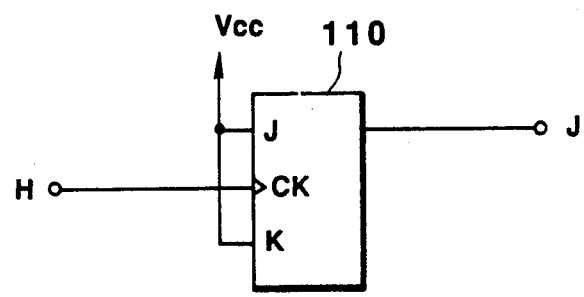

In the above mentioned control circuit 100, the control signal J can be made from the Z phase output H by a simple JK-FF as is shown in FIG. 4. In this circuit, a source voltage is applied to the J input and K input of the JK-FF 110 and the signal H is applied to the clock input. Therefore, the output of this JK-FF 110 will be the control signal J reversely rotating when the signal H rises.

Figure 5:
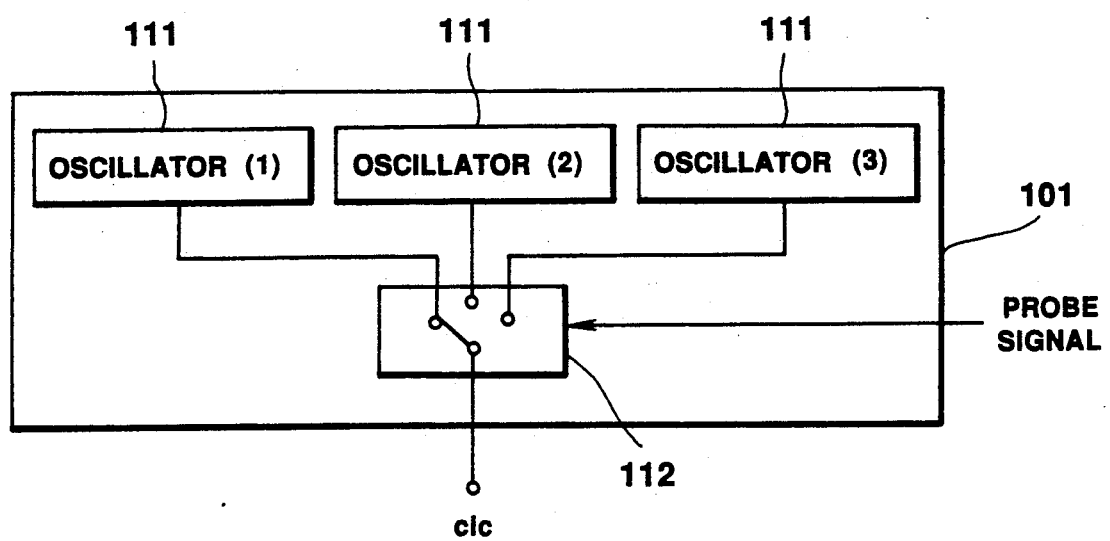

Now, in this embodiment, as shown in FIG. 5, the above mentioned clock oscillator 101 has a plurality of oscillators 111 outputting clocks different in the frequency from one another and the clock of any of these oscillators can be output through a switching switch 112 which is switched by a probe signal corresponding to the kind of the probe.

Figure 6:
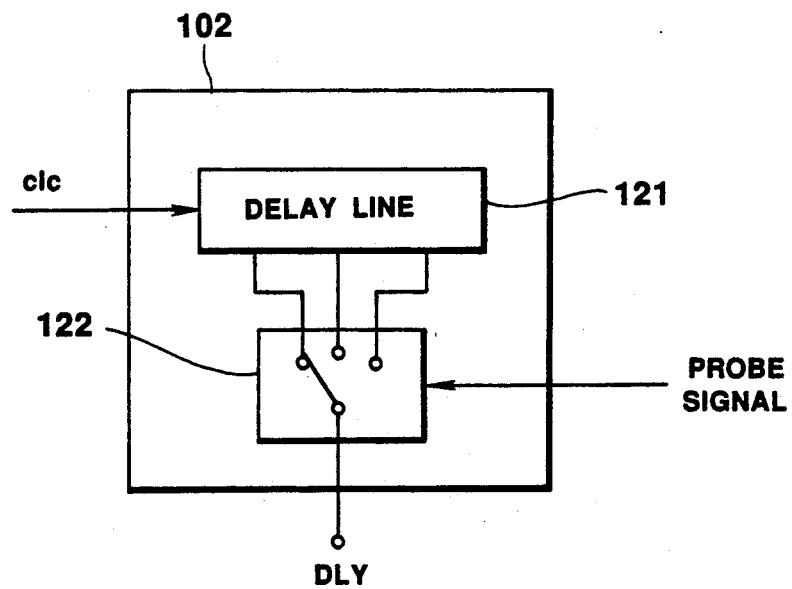

As shown in FIG. 6, the above mentioned delaying circuit 102 has a delay line 121 fitted with a plurality of taps so that any of a plurality of outputs different in the delay amount from one another of this delay line 121 may be output through a switching switch 122 which is switched by a probe signal corresponding to the kind of the probe. The delay amount of each output of the above mentioned delay line 121 is ¼ of the period of the clock of each of the above mentioned oscillators 111 and the switching switches 112 and 122 are switched as operatively connected so that the period of the clock of the oscillator 111 and the delay amount by the delay line 121 may correspond to each other.

Thus, by varying frequencies of the clock clc from the clock oscillator 101 and the signal DLY from the delaying circuit 102, the rotating speeds, that is, the scanning speeds of the rotary motion part (1) 8 and rotary motion part (2) 13 can be varied.

The case of varying the scanning speed shall be explained in the following with reference to FIGS. 7(a)–7(e).

Figure 7A:
FIGS. 7(a)-7(e) are waveform diagrams for explaining the case of changing the scanning speed.
Figure 7B:
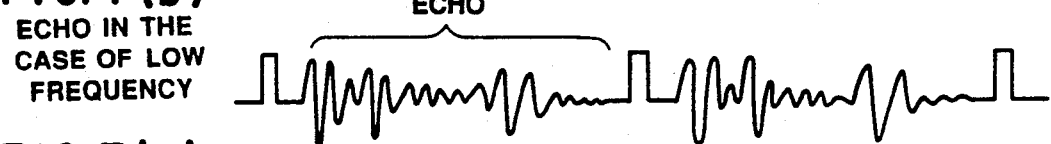
Figure 7C:

A characteristic of ultrasonic waves, the lower the frequency, the farther it travels and the higher the frequency the sooner it attenuates and the shorter the distance it travels. Therefore, for the signal transmitting pulse (ultrasonic wave) of a period as is shown in FIG. 7(a), in case the frequency of the signal transmitting pulse is low, the echo will be long as shown in FIG. 7(b) but, on the other hand, in case the frequency of the signal transmitting pulse is high, the echo will be short as shown in FIG. 7(c). This is because the echo from a long distance will attenuate and will not return.

Figure 7D:
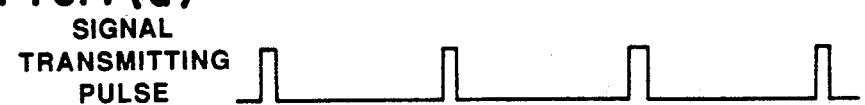
Figure 7E:
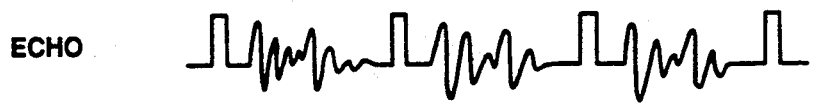

Therefore, when the attenuation of the frequency is considered, in case an ultrasonic wave of a low frequency is used, it will be necessary to see a long distance and the scanning speed had better be low. On the other hand, in case an ultrasonic wave of a high frequency is used, the scanning speed will be able to be elevated. That is, even if the period of the signal transmitting pulse is made short as shown in FIG. 7(d), the echo will be able to be well received.

Therefore, in case the frequency of the ultrasonic wave is varied by replacing the ultrasonic probe, in order to obtain the optimum frame rate, it will be necessary to make the scanning speed correspond to that frequency.

Thus, according to this embodiment, by the rotation, advance and retreat of the vibrator 1, a radial image and linear image can be obtained, the rotary motion and advancing and retreating motion are synchronized with each other and therefore, even if the scanning speed is varied, the relative speed of the rotation, advance and retreat will not vary and a radial image and linear image always stabilized under fixed conditions in relation with each other will be able to be obtained. That is, the resolution (diagnosing distance) of the linear image will not vary and the diagnosing part of the radial image also will not vary.

In this embodiment, the detecting output of the position detector (1) 9 may be made a driving signal of the rotary motion part (2) 13.

Figure 8:
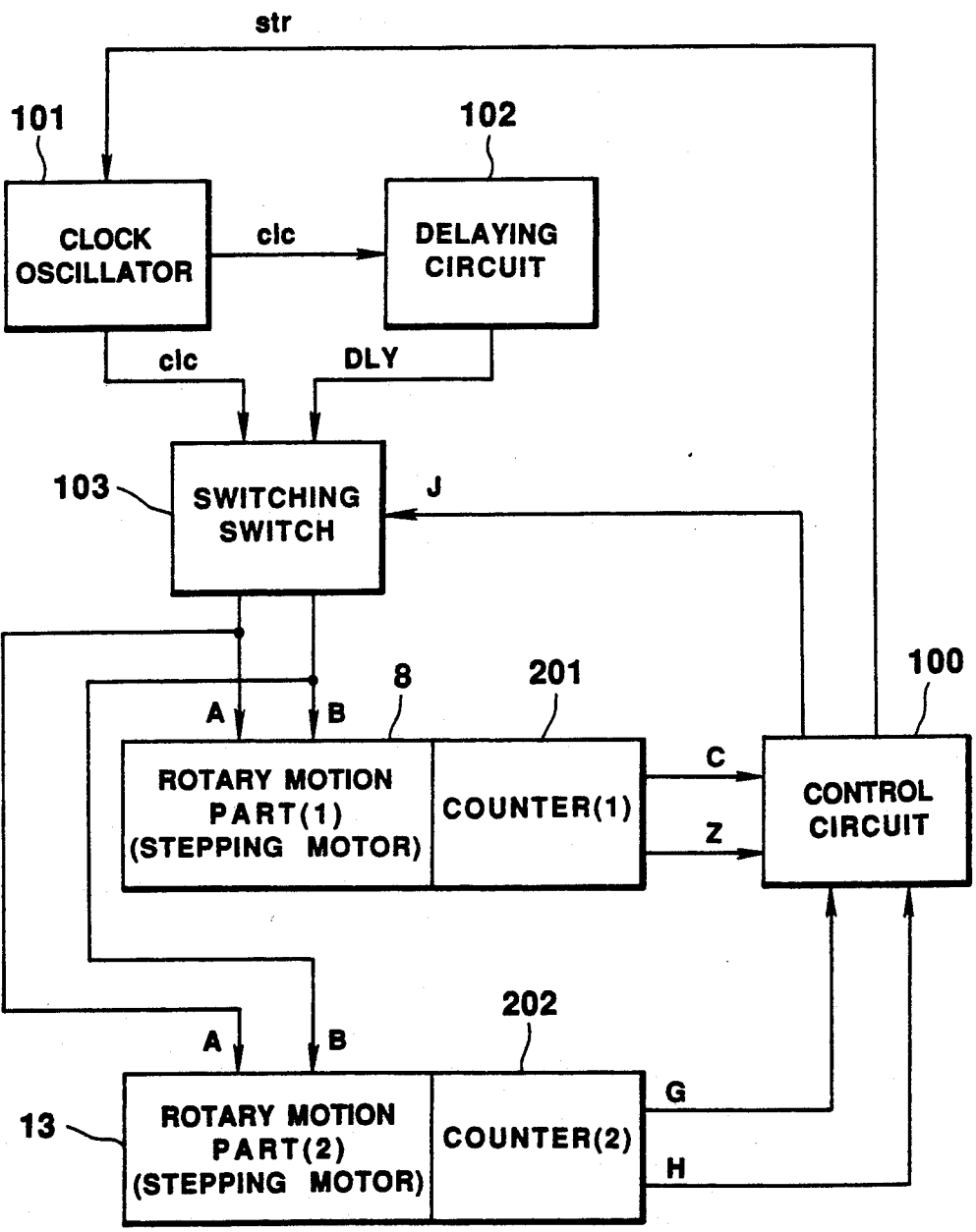
FIG. 8 is a block diagram showing an ultrasonic probe controlling system in the second embodiment of the present invention.

In FIG. 8 is shown the second embodiment of the present invention.

In this embodiment, counters 201 and 202 are used instead of the encoders of the position detectors (1) 9 and (2) 14 in the first embodiment. These counters 201 and 202 respectively count the clocks clc input into the stepping motors and will output them as signals Z and H to the control circuit 100 if the clocks clc are counted, for example, to be 10. The same as in the first embodiment, the control circuit 100 makes a control signal J from the above mentioned signal H or Z and thereby switches the switching switch 103. Either one of the counters 201 and 202 will do.

The other formations, operations and effects are the same as in the first embodiment.

Figure 9:
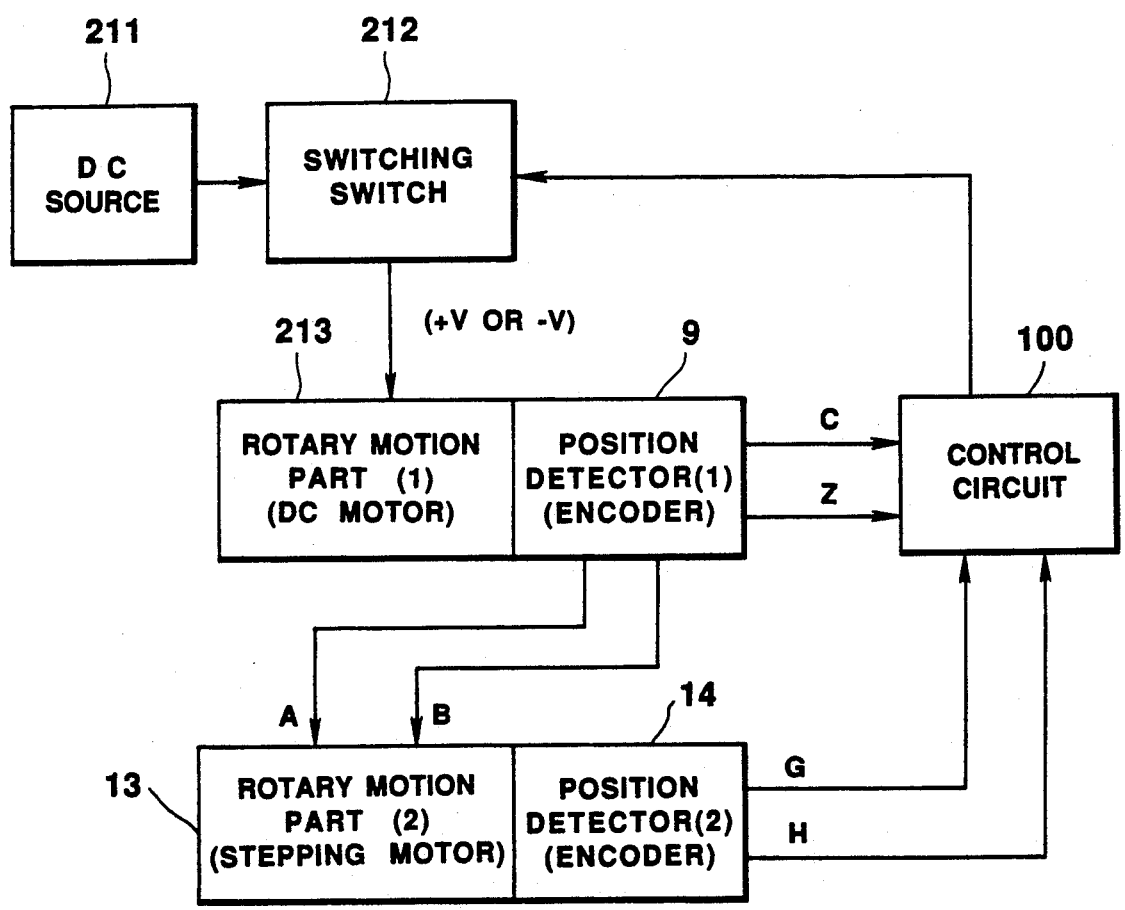
FIG. 9 is a block diagram showing an ultrasonic probe controlling system in the third embodiment of the present invention.

In FIG. 9 is shown the third embodiment of the present invention.

In this embodiment, a DC motor 213 is used instead of the stepping motor of the rotary motion part (1) in the first embodiment.

A direct current voltage of +V or −V is applied to the above mentioned DC motor 213 from a direct current (DC) source 211 through a switching switch 212 which is switched by the control circuit 100. The above mentioned DC motor 213 will rotate normally when the applied voltage is +V but will rotate reversely when the applied voltage is −V. The rotating position of the above mentioned DC motor 213 is detected by the encoder of the position detector (1) 9 and the signals of the A phase and B phase output from this encoder are input into the stepping motor of the rotary motion part (2) 13. Thereby, the stepping motor of the rotary motion part (2) 13 rotates as synchronized with the DC motor of the rotary motion part (1).

Also, when the direct current level applied to the above mentioned rotary DC motor 213 is varied, the rotating speed of the DC motor 213 will vary and, in response to it, the rotating speed of the stepping motor of the rotary motion part (2) 13 will also vary.

The other formations, operations and effects are the same as in the first embodiment.

In FIGS. 10 and 11(a)–11(b) is shown the fourth embodiment of the present invention.

In the first embodiment, the rotary motion part (1) 8 and rotary motion part (2) 13 are driven by clocks of the same period but the period may be different. In this embodiment, the driving frequency of the rotary motion part (2) 13 is lower than the driving frequency of the rotary motion part (1), the output signals A and B of the switching switch 103 are input into a frequency divider 221 and the signals A' and B' having had the frequency divided are input into the rotary motion part (2) 13. FIG. 11(a) shows the signal A and FIG. 11(b) shows the signal A' obtained by dividing the frequency of the signal A, for example, to be ½.

Even if the signal thus having had the frequency divided is used, the rotary motion part (1) 8 and rotary motion part (2) 13 will be synchronized.

In this embodiment, the detecting output of the position detector (1) 9 may have the frequency divided and may be input into the rotary motion part (2) 13.

The other formations, operations and effects are the same as in the first embodiment.

Figure 12:
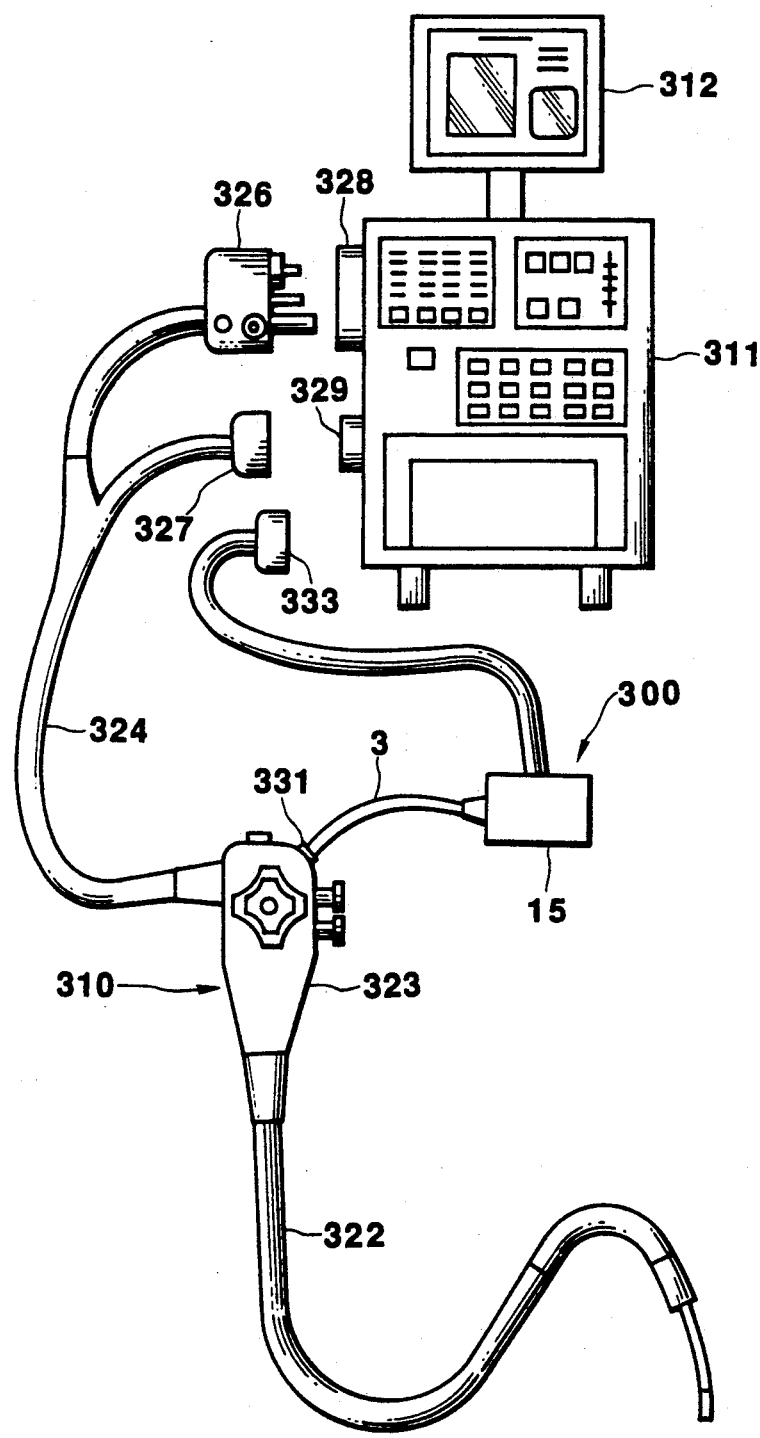
FIG. 12 is an elevation showing an ultrasonic video scope system in the fifth embodiment of the present invention.

In FIG. 12 is shown the fifth embodiment of the present invention.

In this embodiment, an ultrasonic probe 300 having had the drive transmitting part and outer tube 3 made flexible can be inserted into a body cavity through a channel in the endoscope.

An ultrasonic video scope system shown in FIG. 12 comprises an ultrasonic video scope 310, an observing apparatus 311 integrating a video scope observing apparatus and ultrasonic observing apparatus to which this ultrasonic video scope 310 is connected and a monitor 312 connected to the above mentioned observing apparatus 311. The above mentioned ultrasonic video scope 310 has an elongate flexible insertable part 322, an operating part 323 connected to this insertable part 322 at the rear end and a universal cord 324 extended from the above mentioned operating part 323 on the side. This universal cord 324 is branched on the end side into two branches and is provided on one branch with a video scope connector 326 and on the other branch with an ultrasonic connector 327. The above mentioned video scope connector 326 and ultrasonic connector 327 are to be connected respectively to a video scope connector receptacle 328 and ultrasonic connector receptacle 329 provided in the observing apparatus 311.

An illuminating window, optical observing window and ultrasonic observing window are provided in the tip part of the above mentioned insertable part 322. Inside the above mentioned illuminating window, there is provided a light distributing lens to which at the rear end a light guide is connected. This light guide is inserted through the insertable part 322, operating part 323 and universal cord 324 and is connected to the video scope connector 326 which is to be connected to the connector receptacle 328 so that the illuminating light emitted from a light source within the observing apparatus 311 may enter the above mentioned light guide at the entrance end. Inside the above mentioned optical observing window, an objective lens system is provided and a solid state imaging device such as a CCD is arranged in the image forming position of this objective lens system and is connected to an optical image signal processing circuit within the observing apparatus 311 through signal lines inserted through the insertable part 322, operating part 323 and universal cord 324 and connected to the video scope connector 326. Also, inside the above mentioned ultrasonic observing window, an ultrasonic vibrator is provided and is connected to an ultrasonic image signal processing circuit within the observing apparatus 311 through signal lines inserted through the insertable part 322, operating part 323 and universal cord 324 and connected to the ultrasonic conector 327. The above mentioned optical image signal processing circuit and ultrasonic image signal processing circuit respectively process signals for the solid state imaging device and ultrasonic vibrator and output a video signal of the optical image and video signal of the ultrasonic image. These video signals of the optical image and ultrasonic image are synthesized to be output to a monitor 312 in which the optical image and ultrasonic image are displayed.

Within the above mentioned insertable part 322 a treating instrument channel is formed and opens on the tip side in the insertable Part 322 at the tip and on the rear end side in an inserting port 331 provided in the operating part 323.

In such an ultrasonic video scope, in the case of using the ultrasonic probe 300, the ultrasonic probe 300 is inserted into the treating instrument channel through the inserting port 331 of the ultrasonic video scope 310 and is projected on the tip side out of the ultrasonic video scope 310 on the tip side. Also, the ultrasonic connector 333 provided on the ultrasonic probe 300 is connected to the ultrasonic connector receptacle 329 of the observing apparatus 311. By driving this ultrasonic probe 300, the optical image obtained by the ultrasonic video scope 310 and the ultrasonic image obtained by the ultrasonic probe 300 can be displayed in the monitor 312.

The video scope observing apparatus and ultrasonic observing apparatus may not be integral with each other.

Also, the ultrasonic probe 300 may be inserted through the treating instrument channel of the video scope to display the optical image and ultrasonic image in the monitor or may be inserted through the treating instrument channel of an optical endoscope (fiber scope). In the case of using the optical endoscope, an externally fitted television camera may be connected to the eyepiece part to display on the monitor the optical image and ultrasonic image photographed by this television camera.

The formation and operation of the ultrasonic probe 300 are the same as in the first to fourth embodiments.

In the first to fifth embodiments, an ultrasonic mirror fixing the vibrator, reflecting and emitting toward the observed part the ultrasonic wave issued from this vibrator and reflecting and transmitting to the vibrator the echo from the observed part may be provided and may be rotated, advanced and retreated.

The two scanning systems to be synchronized are not limited to the radial scanning and linear scanning but may be a combination of the sector scanning and linear scanning.

In FIGS. 13 to 20 is shown the sixth embodiment of the present invention.

First of all, the formation of the control system of the ultrasonic observing apparatus of this embodiment shall be explained with reference to FIG. 13.

In this ultrasonic observing apparatus, an elongate ultrasonic probe 501 to be inserted into a body cavity is provided at the tip with an ultrasonic vibrator 502 to be an ultrasonic wave transmitting and receiving part generating diagnosing ultrasonic waves and receiving echos from the observed part and is connected at the rear end to a driving part 503.

The above mentioned driving part 503 comprises an advancing and retreating motion motor 504 advancing and retreating the ultrasonic probe 501, an advancing and retreating position detector 505 detecting the position in the advancing and retreating direction of the ultrasonic probe 501, a rotary motion motor 506 rotating the ultrasonic probe 501, a rotary encoder 507 detecting the position in the rotating direction of the ultrasonic probe 501, a linearly scanned section position designating means 508 and a radiallly scanned section position designating means 509.

The above mentioned ultrasonic vibrator 502 is connected through a cable 510 to a signal transmitting and receiving switching circuit 511 within the observing apparatus not illustrated. This signal transmitting and receiving switching circuit 511 is connected to a pulser circuit 512 generating signal transmitting pulses and an amplifying circuit 513 amplifying the received signals. The above mentioned amplifying circuit 513 is connected to a linearly scanning signal extracting circuit 514 and radially scanning signal extracting circuit 515. The above mentioned linearly scanning signal extracting circuit 514 is connected to a linearly scanned section positiion designating means 508 and the above mentioned radially scanning signal extracting circuit 515 is connected to a radially scanned section positiion designating means 509. The output of the above mentioned linearly scanning signal extracting circuit 514 is input into a linearly scanning DSC (digital scan converter) 516 and the output of the above mentioned radially scanning signal extracting circuit 515 is input into a radially scanning DSC 517. The above mentioned linearly scanning DSC 516 and radially scanning DSC 517 are connected to a monitor 519 through a DSC switching circuit 518 so that the output of one of the DSC 516 and 517 may be input into this monitor 519 and may be displayed on the monitor 519.

The formation of the ultrasonic observing apparatus driving system of this embodiment shall be explained in the following with reference to FIG. 14.

The ultrasonic probe 501 provided in the tip part with the ultrasonic vibrator 502 is covered with a protective tube 520 transmitting ultrasonic waves, is inserted on the rear end side into a driving part 503, is held in the driving part 503 by a holding 521 provided within this driving part 503 and is further held by bearings 522 in a housing 523 provideed within the driving part 503.

Within the above mentioned housing 523, a gear (1) 524 is fitted to the ultrasonic probe 501 and is meshed with a gear (2) 525 fitted to the shaft of the rotary motion motor 506. The above mentioned rotary motion motor 506 is fixed within the housing 523 so that the ultrasonic probe 501 may be rotated through the gears (2) 525 and (1) 524 by the rotation of this rotary motion motor 506. The above mentioned rotary motion motor 506 is fitted with a rotary encoder 507 by which the rotating position of the ultrasonic probe 501 may detected.

Figure 19:
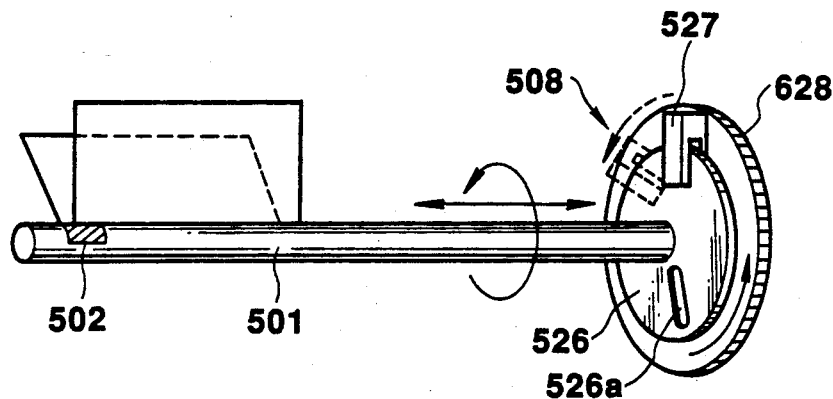

Also, the linearly scanned section position designating means 508 formed as in the following is provided within the above mentioned housing 523. That is to say, as shown in FIG. 19, a disc 526 provided with a slit 526a is fitted to the ultrasonic probe 501 within the housing 523 and a photointerrupter (1) 527 is provided to hold this disc 526. As shown in FIG. 14, the above mentioned photointerrupter (1) 527 is fixed to a disc 620 through which the ultrasonic probe 501 is inserted and in the center part of which a gear 621 is fixed. A gear 622 is meshed with this gear 621 and is fitted with a linearly scanned section position designating rod 528 which is projected at the end out of the outer fitting 503a of the driving part 503 and is provided with a grip 528a. By rotating this grip 528a, the above mentioned photointerrupter (1) 527 can be moved through the gears 622 and 621 an disc 620.

A linearly scanned section position designating dial 628 may be provided as shown in FIG. 19 instead of the above mentioned disc 620, gears 621 and 622 and linearly scanned section position designating rod 528. The above mentioned photointerrupter (1) 527 is fixed to this dial 628 which is projected in a part out of the outer fitting 503a of the driving part 503 so that, by rotating this dial 628, the above mentioned photointerrupter (1) 527 may be moved.

Figure 13:
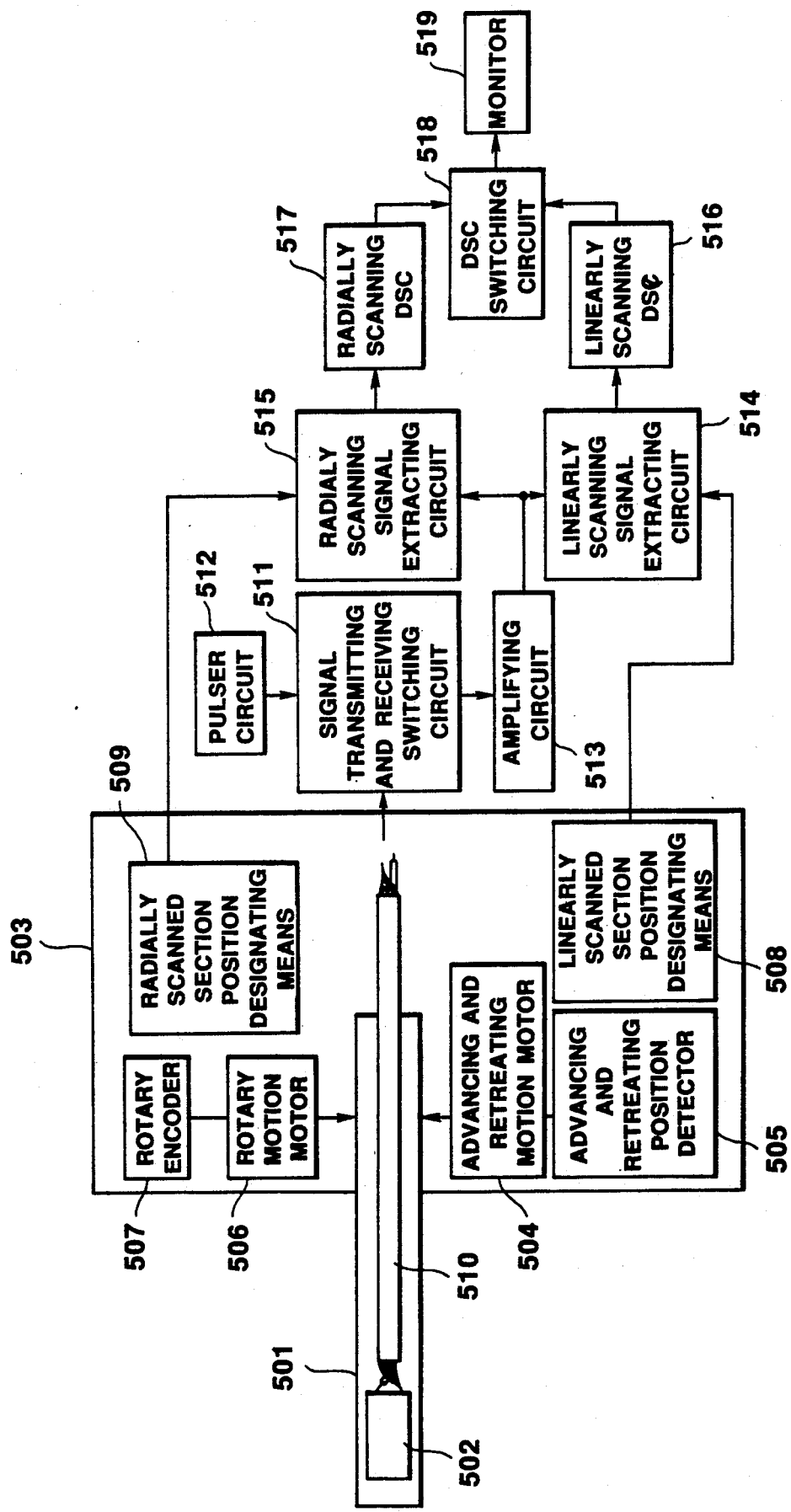

The output of the above mentioned photointerrupter (1) 527 is input into the linearly scanning signal extracting circuit 514 shown in FIG. 13.

The above mentioned ultrasonic probe 501 is connected at the final end with a rotary connector 529 and a cable 530 connected to this rotary connector 529 is connected to the signal transmitting and receiving switching circuit 511 in FIG. 13.

The above mentioned housing 523 is fixed by a fixing member 531 which is screwed with a ball screw 532 conected to the shaft of the advancing and retreating motion motor 504. The above mentioned advancing and retreating motion motor 504 is fixed to the outer fitting 503a of the driving part 503 so that, by the rotation of this advancing and retreating motion motor 504, the ball screw 532 may be rotated, thereby the fixing member 531 may be advanced and retreated and the ultrasonic probe 501 may be advanced and retreated. The above mentioned advancing and retreating motion motor 504 is fitted with an advancing and retreating position detector 505 by which the advancing and retreating position of the ultrasonic probe 501 may be detected.

Also, within the above mentioned driving part 503, a radially scanned section position designating means 509 formed as in the following is provided, that is, the above mentioned fixing member 531 is fitted with a slit plate 533 provided with a slit 533a and a photointerrupter (2) 534 is arranged to hold this slit plate 533. This photointerrupter (2) 534 moves in the axial direction of the ultrasonic probe 501 as operatively connected with a slide volume 535 slidably provided in the outer fitting 503a of the driving part 503.

The output of the above mentioned photointerrupter (2) 534 is input into the radial scanning signal extracting circuit 515 shown in FIG. 13.

The operation of this embodiment shall be explained in the following.

The signal transmitting pulse generated from the pulser circuit 512 is fed to the ultrasonic vibrator 502 through the cable 510 from which an ultrasonic pulse is emitted. The echo from the observed part by this ultrasonic pulse is received by the above mentioned ultrasonic vibrator 502. This received signal is input into the amplifying circuit 513 through the cable 510 and signal transmitting and receiving switching circuit 511. The received signal amplified by this amplifying circuit 513 is input into the linearly scanning signal extracting circuit 514 and radially scanning signal extracting circuit 515 and the received signal of only the designated cross-section is extracted. This extracted received signal is stored in the linearly scanning DSC 516 and radially scanning DSC 517 and is read out of these DSC 516 and 517 as a video signal. The output video signal of one of the DSC 516 and 517 is selected by the DSC switching circuit 518 and is input into the monitor 519 on which an ultrasonic image is displayed.

Figure 14:
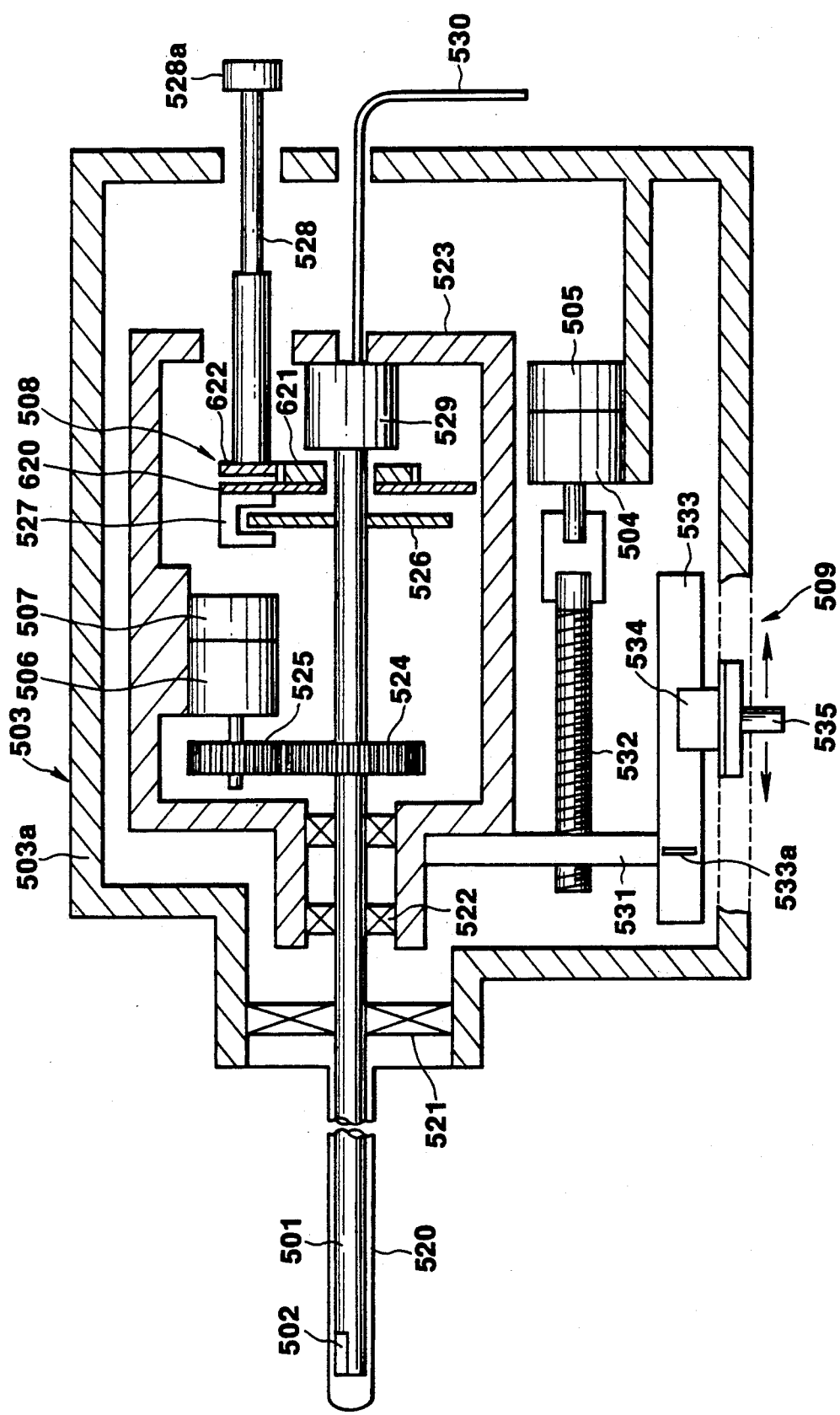

In such mechanism as is shown in FIG. 14, when the advancing and retreating motion motor 504 is driven, the ultrasonic probe 501 will advance or retreat in the inserting axial direction and, when the rotary motion motor 506 is driven, the ultrasonic probe 501 will rotate. When the above mentioned advancing and retreating motion motor 504 and rotary motion motor 506 are simultaneously driven, the ultrasonic probe 501 will simultaneously advance or retreat and rotate. In such state, when the ultrasonic wave is transmitted and received, such columnar scanning as is shown in FIG. 15 will be made.

Figure 15:
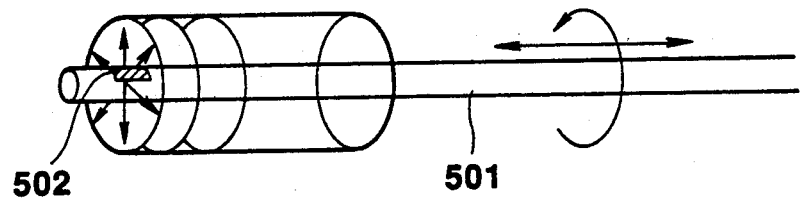

A method of obtaining a linearly scanned image of a designated cross-section by such columnar scanning as is shown in FIG. 15 shall be explained in the following.

As shown in FIG. 19, the ultrasonic probe 501 is fitted with a disc 526 so that, when the ultrasonic probe 501 rotates, whenever a slit 526a provided in this disc 526 passes, a pulse will be output from the photoinerrpter (1) 527. The pulse output of this photointerrupter (1). 527 is input into the linearly scanning signal extracting circuit 514.

Figure 16:
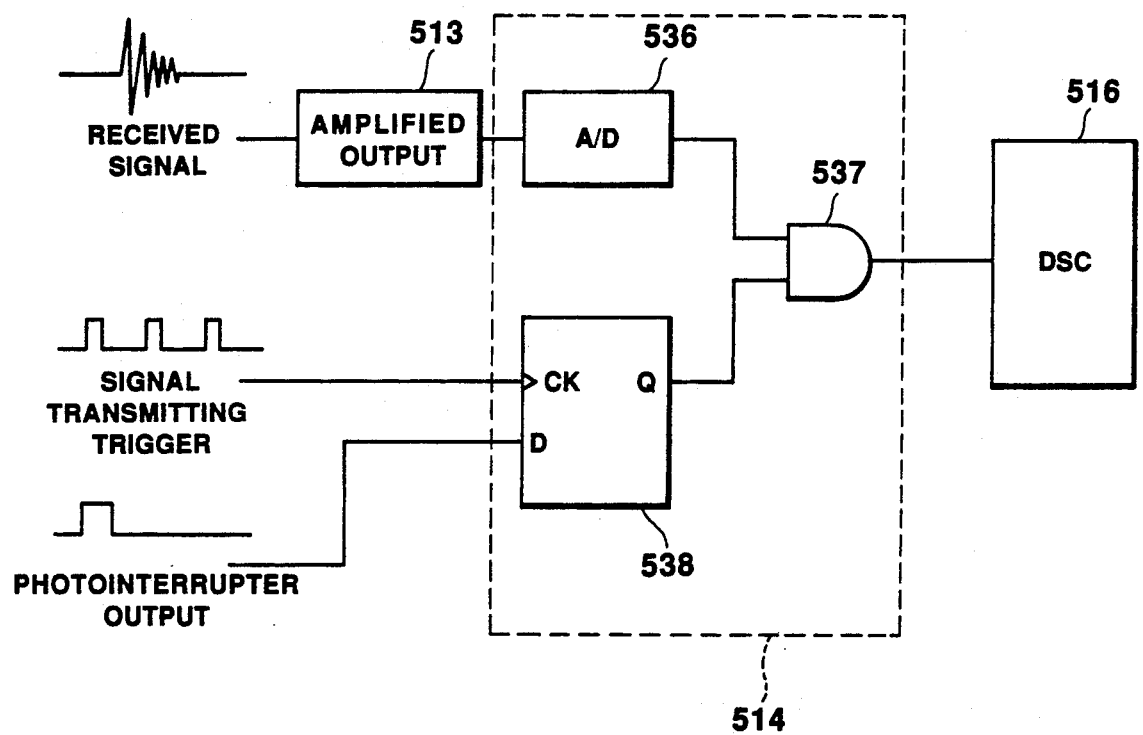

Here, the formation of the linearly scanning signal extracting circuit 514 is shown in FIG. 16 and its operation shall be explained with reference to FIG. 18.

Figure 17:
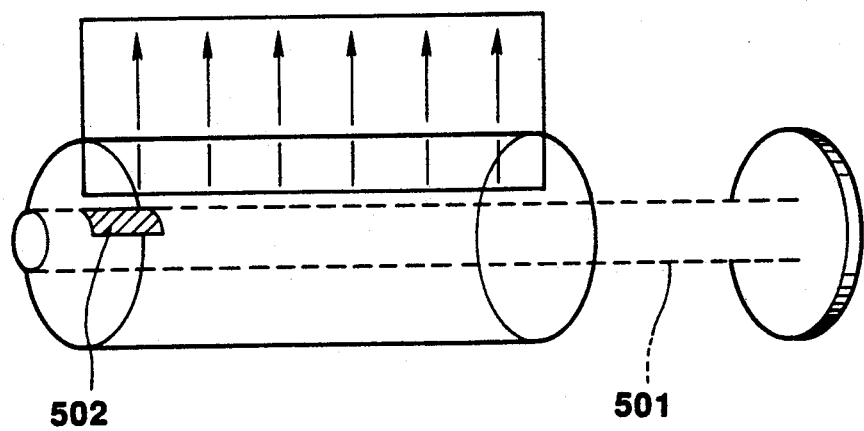

Such a received signal as is shown in FIG. 18(a) is amplified by the amplifying circuit 513 as shown in FIG. 16, is then A/D-converted by an A/D converter 536 and is input into one input end of an AND gate 537. On the other hand, such output pulse of the photointerrupter (1) 527 as is shown in FIG. 18(c) is input into the D input of a latch circuit 538 having as a clock CK such transmitting trigger as is shown in FIG. 18(b), is converted to a signal of one clock of the signal transmitting trigger as shown in FIG. 18(d) and is output from the Q output. The output of this latch circuit 538 is input into the other input end of the AND gate 537. By this AND gate 537, as shown in FIG. 18(e), a logical sum of the output of the latch circuit 538 and A/D-converted output of the received signal is taken and, as shown in FIG. 17, the received signal of only the designated cross-section vertical to the inserting axial direction is extracted. The same as in the conventional linearly scanning observing apparatus, this extracted received signal is displayed as an image in the monitor 519.

Also, by varying the position of the photointerrupter (1) 527 by such a linearly scanned section position designating rod 528 as is shown in FIG. 14 or such linearly scanned section position designating dial 628 as is shown in FIG. 19, the designated cross-section can be varied.

A method of obtaining a radially scanned image of a designated cross-section from such columnar scanning as is shown in FIG. 15 shall be explained in the following.

When the ultrasonic probe 501 advances or retreats, whenever the slit 533a of the slit plate 533 fixed to the fixing member fixing the housing 523 passes the photointerrupter (2) 534, a pulse will be output from this photointerrupter (2) 534 and will be input into the radially scanning signal extracting circuit 515 of the same formation as of the above mentlioned linearly scanning signal extracting circuit 514 and only the received signal by the radial scanning of the designated cross-section will be extracted. This extracted received signal is displayed as an image on the monitor 519 by the radial scanning DSC 517.

Figure 20:
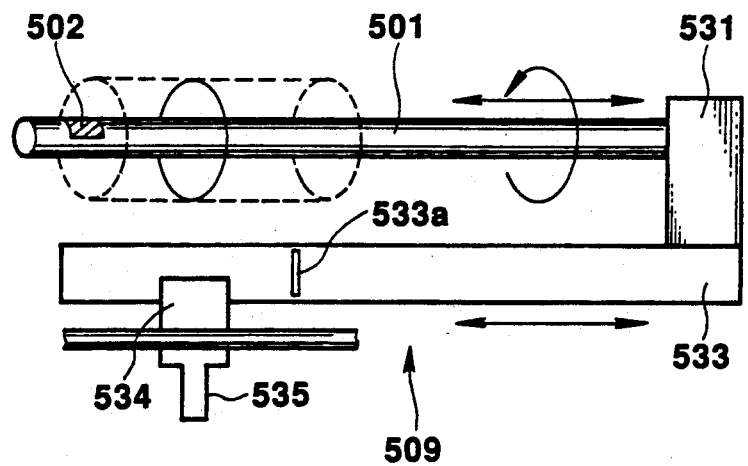

As shown in FIG. 20, as the position of the photointerrupter (2) 534 is movable as operatively connected with the slide volume 535, the designation of the position of the cross-section of this radially scanned image can be determined by the position of this slide volume 535.

Thus, according to this embodiment, by using the photointerrupters 527 and 534, disc 526 having the slit and slit plate 533 for the cross-section position designating mean 508 and 509 and by a cheap and simple circuit formation and mechanism, without stopping any motion of the advance, retreat and rotation of the ultrasonic probe 501, a linearly scanned image or radially scanned image of any position can be obtained.

Also, as required, the linear scanning and radial scanning can be used as switched to each other, therefore the diagnosing time can be reduced and the pain of the patient can be alleviated.

Figure 21:
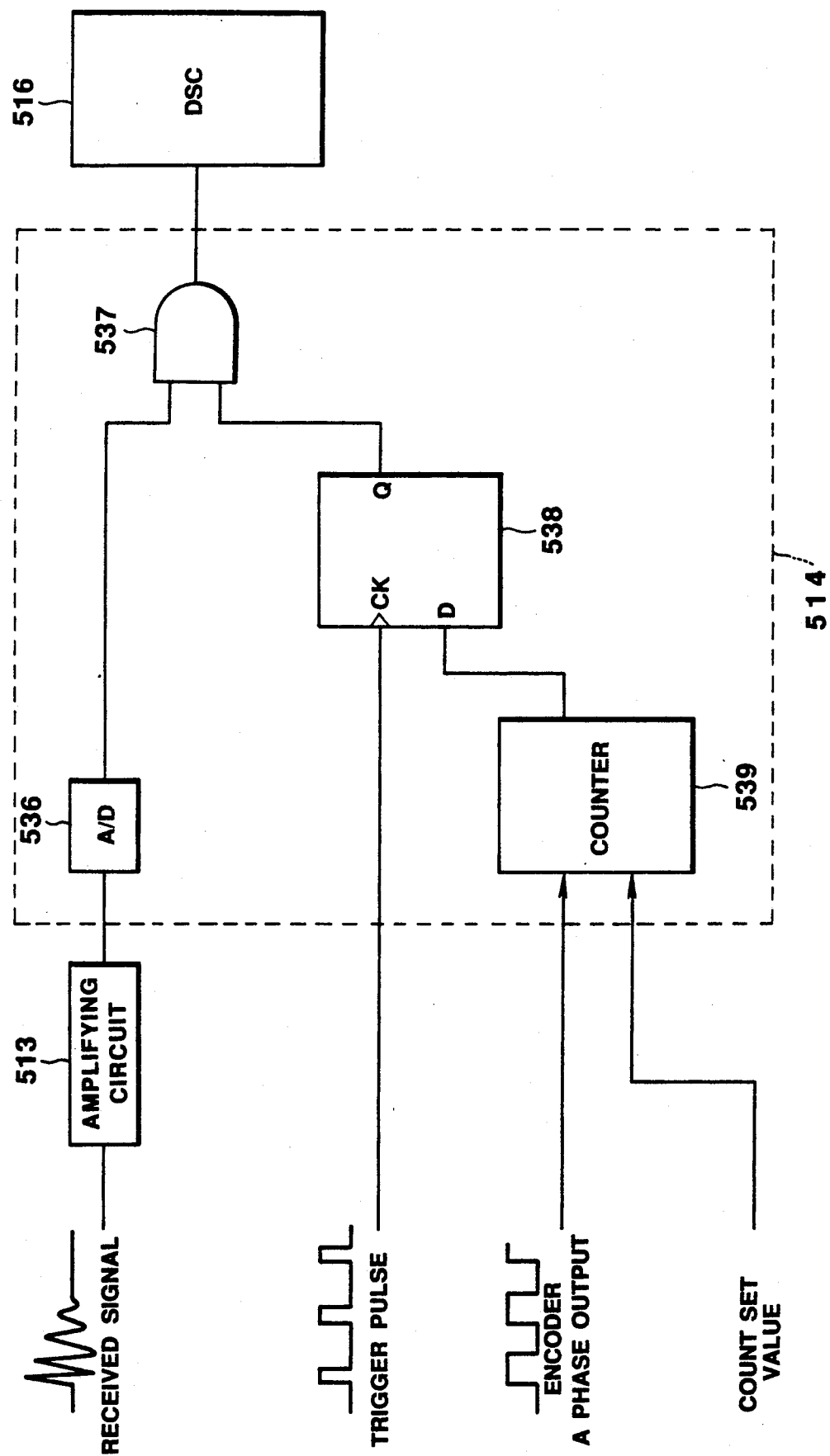
FIG. 21 is a block diagram showing the formation of a signal extracting circuit in the seventh embodiment of the present invention.

In FIG. 21 is shown the seventh embodiment of the present invention.

In this embodiment, as a means of designating the cross-section positions of a linearly scanned image and radially scanned immage, the output pulse of a position detecting encoder is used.

Also, in this embodiment, ultrasonic waves are transmitted and received by simultaneously advancing or retreating and rotating the ultrasonic probe 501. As shown in FIG. 21, a received signal is amplified by the amplifying circuit 513, is then A/D-converted by the A/D converter 536 within the signal extracting circuit 514 and is then input into one input end of the AND gate 537.

The designation of the cross-section position in this embodiment is set as a number of pulses on the basis of the Z phase of the encoder 507. This number of cross-section position designating pulses can be input by the keyboard or the like of the observing apparatus to which the ultrasonic probe 501 is connected.

The above mentioned number of cross-section position designating pulses is input as a count setting value into a counter 539 provided within the above mentioned signal extracting circuit 514. This counter 539 counts the number of pulses of the A phase output of the encoder 507 and will output a counter output pulse when the above mentioned count set value is reached. This cpunter output pulse is input into the latch circuit 538 having a trigger pulse as a clock CK. The same as in the sixth embodiment, a pulse of a length of one clock of the trigger pulse is output from this latch circuit 538 and is input into the other input end of the AND gate 537.

In the above mentioned AND gate 538, the same as in the sixth embodiment, a logical sum of the A/D-converted output of the received signal and the output pulse of the latch circuit 538 is taken and the received signal of only the designated cross-section is extracted.

In FIG. 21, the linearly scanning signal extracting circuit 514 is shown but the formation and operation of the radially scanning signal extracting circuit 515 are also the same.

As such means of designating the positions of the cross-sections of a linearly scanned image and radially scanned image is provided, the cross-section designating means 508 and 509 in the sixth embodiment will be unnecessary.

Thus, according to this embodiment, if the relation of the number of pulses and cross-section image is known in advance, even if there is no particular designating mechanism, a tomographic image of any position will be able to be obtained.

The other formations, operations and effects are the same as in the sixth embodiment.

Figure 22:
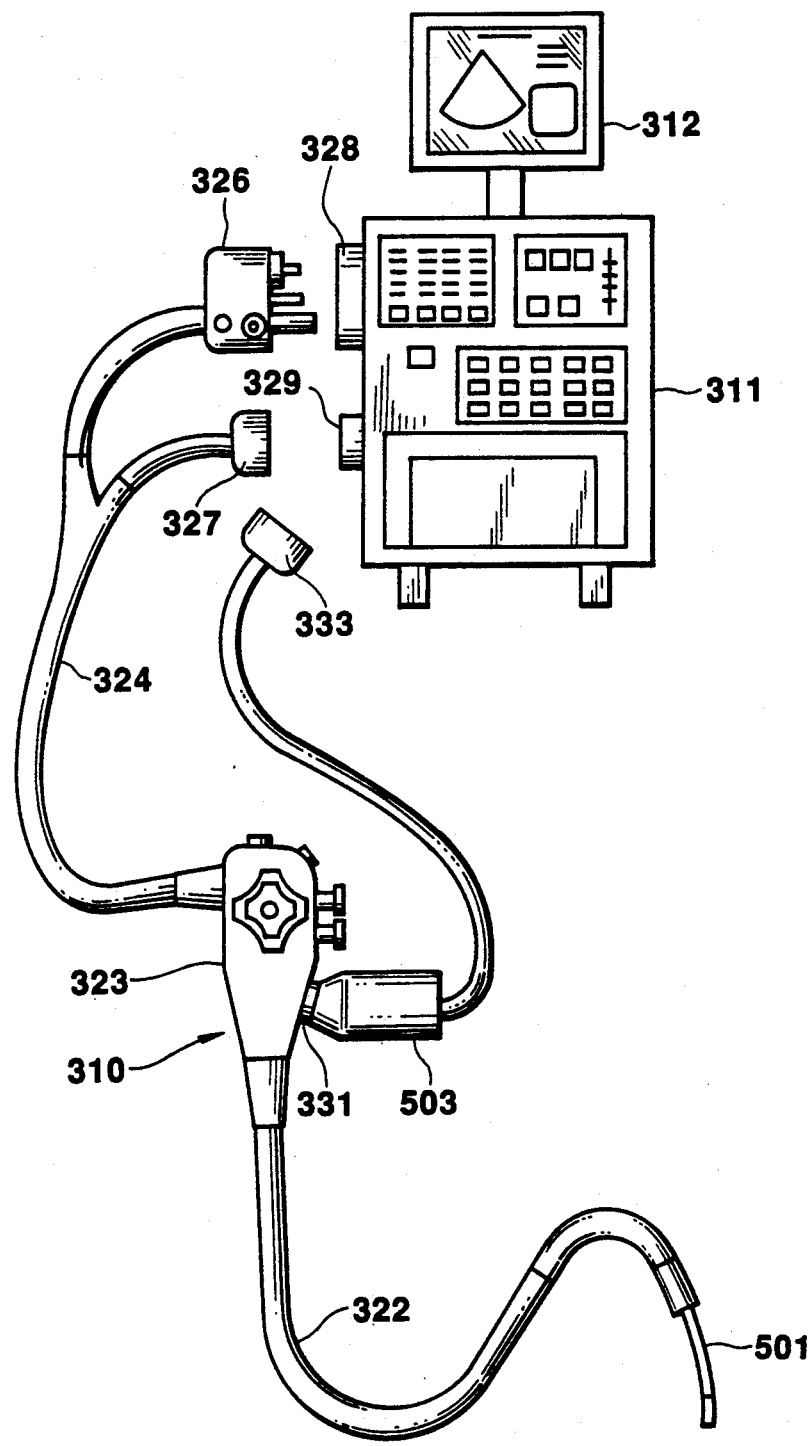
FIG. 22 is an elevation showing an ultrasonic video scope in the eighth embodiment of the present invention.

In FIG. 22 is shown the eighth embodiment of the present invention.

In this embodiment, the ultrasonic probe 501 is made flexible so as to be able to be inserted into a body cavity through a channel in the endoscope.

The ultrasonic video scope system shown in FIG. 22 comprises an ultrasonic video scope 310, an observing apparatus 311 to which this ultrasonic video scope 310 is connected and in which a video scope observing apparatus and ultrasonic observing apparatus are integrated and a monitor 312 connected to the above mentioned observing apparatus 311. The above mentioned ultrasonic video scope 310 is of the same formation as of the ultrasonic video scope 310 of the fifth embodiment except that the position of the inserting port 331 of the instrument channel is different. Also, the formation of the observing apparatus 311 is the same as of the observing apparatus 311 of the fifth embodiment.

In such an ultrasonic video scope, in case the ultrasonic probe 501 is to be used, the ultrasonic probe 501 is inserted into the treating instrument channel through the inserting port 331 in the ultrasonic video scope 310 and is projected on the tip side out of the ultrasonic video scope 310 on the tip side. The driving part 503 connected to the ultrasonic probe 501 is fixed to the inserting port 331. The ultrasonic connector 333 connecrted to the above mentioned ultrasonic probe 501 is connected to the ultrasonic connector receptacle 329 of the observing apparatus 311. By driving this ultrasonic probe 501, an optical image obtained by the ultrasonic video scope 310 and an ultrasonic image obtained by the ultrasonic probe 501 can be displayed in the monitor 312.

Thus, according to this embodiment, by inserting the ultrasonic probe 501 into the treating instrument channel, the ultrasonic probe 501 can be inserted also into a fine body cavity and, without moving the ultrasonic probe 501, a linear image and radial image can be obtained.

The ultrasonic probe 501 may be inserted into the treating instrument channel in a video scope to display an optical image and ultrasonic image in the monitor or may be inserted into the treating instrument channel in an optical endoscope (fiber scope). In the case of using an optical endoscope, an externally fitted television camera may be connected to the eyepiece part so that an optical image and ultrasonic image imaged by this television camera may be displayed in the monitor.

The other formations, operations and effects are the same as in the sixth or seventh embodiment.

In the sixth to eighth embodiments, an ultrasonic mirror fixing the vibrator, reflecting an ultrasonic wave issued from this vibrator, emitting the ultrasonic wave toward a part to be observed, reflecting an echo from the observed part and transmitting the echo to the vibrator may be provided an may be rotated, advanced and retreated.

Also, two monitors may be prepared to be used respectively for a radially scanned image and linearly scanned image so that the two images may be simultaneously observed.

Thus, according to the sixth to eighth embodiments, there are provided a driving means for simultaneously advancing or retreating and rotating an ultrasonic wave transmitting and receiving part, a designating means for designating the position of a cross-section to be scanned to obtain a tomographic image and a signal extracting means for extracting only the received signal from the ultrasonic wave transmitting and receiving part on the cross-section designated by this designating means and therefore there is an effect that, with a simple formation, a linearly scanned image and radially scanned image of any position can be obtained while simultaneously advancing or retreating and rotating the ultrasonic wave transmitting and receiving part.

In FIGS. 23 to 26 is shown the ninth embodiment of the present invention.

Figure 23:
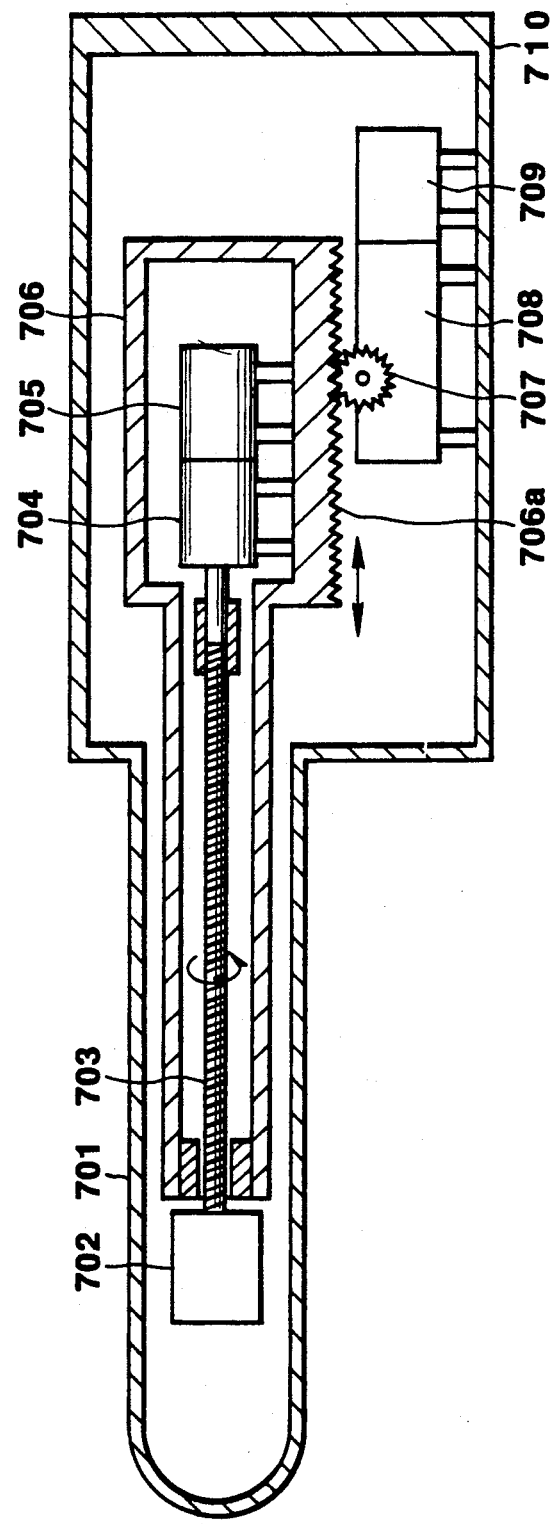

FIG. 23 shows an essential part relating to the ninth embodiment of the present invention wherein an ultrasonic vibrator 702 is provided at the tip of an insertable part 701 into a body cavity and is connected to the tip of a flexible shaft 703 extended through the insertable part 701. The flexible shaft 703 is rotated by the driving force of a motor 704 to rotate the ultrasonic vibrator 702 so that a radial scanning may be possible. The rotation amount of the motor 704 can be sensed by an encoder 705. The motor 704 and encoder 705 are fixed to a supporter 706 so as to be able to advance and retreat in the axial direction of the insertable part 701 through a later described moving means together with the above mentioned flexible shaft 703 and ultrasonic vibrator 702.

A rack 706a is formed on one side surface in the direction intersecting at right angles with the moving direction of the supporter 706 which can be moved by this rack 706a and a pinion 707 meshing with the rack 706a. This pinion 707 can be rotated by the driving force of the motor 708. The rotation amount of the motor 708 is sensed by an encoder 709. The motor 708 and encoder 709 are fixed to an outer fitting body 710 internally fitting the whole including the above mentioned suppporter 706 so that the above mentioned ultrasonic vibrator 702 ma be rotated through the flexible shaft 703 and may be advanced and retreated through the rack 706a and pinion 707.

Figure 24:
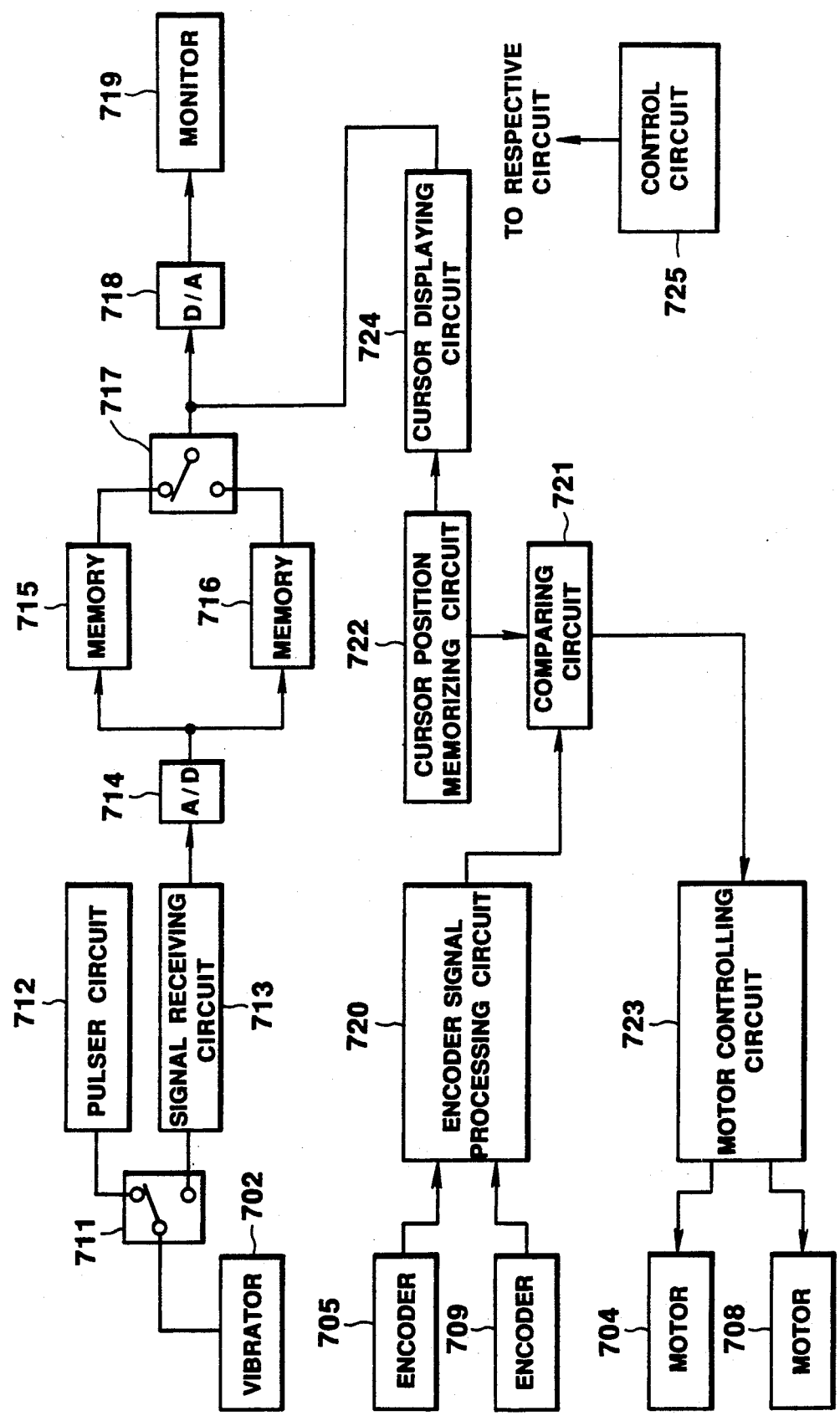

FIG. 24 is a block diagram showing the whole of an ultrasonic observing apparatus. The ultrasonic vibrator 702 is connected to a pulser circuit 712 through a switch 711 and is connected to a signal receiving circuit 713. The signal from the signal receiving circuit 713 is converted to a digital signal by an A/D converter 714 and is input into memories 715 and 716. The outputs from the memories 715 and 716 are input into a D/A converter 718 through a switch circuit 717 and are converted to an analogue signal which is then displayed in a monitor 719.

On the other hand, the signals from the encoders 705 and 709 are input into an encoder signal processing circuit 720, are then compared through a comparing circuit 721 with a value held in a cursor position memorizing circuit 722 and are input into a motor controlling circuit 723 to rotate the motors 704 and 708. The value of the cursor position memorizing circuit 722 is displayed in the monitor 719 as superimposed on the images from the memories 715 and 716 through the D/A converter 718 by the cursor position memorizing circuit 722. The reference numeral 725 represents a control circuit controlling the above mentioned respective circuits.

Figure 25:
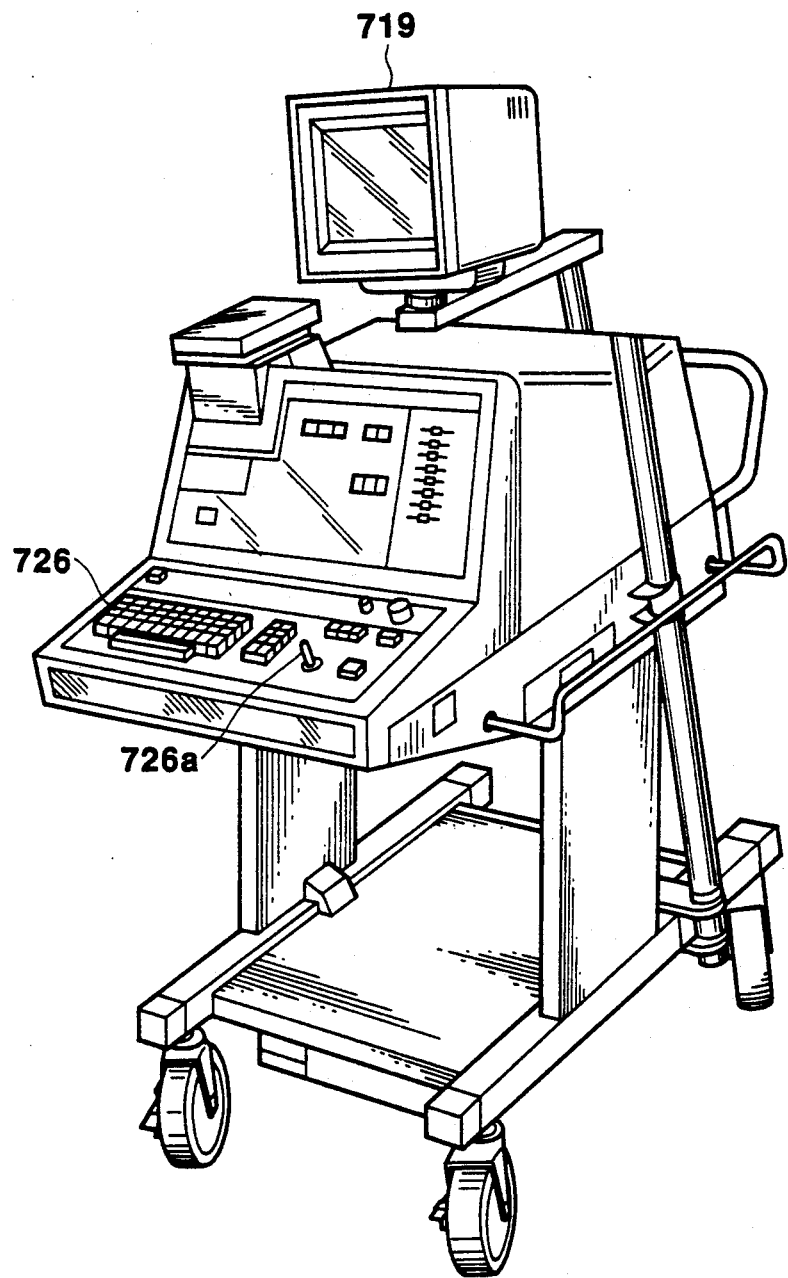

FIG. 25 shows the appearance of the ultrasonic observing apparatus wherein the radial scanning and linear scanning can be switched to each other by a switching switch on an operating panel 726 and the respective scanning images are displayed on the monitor 719 positioned above the operating panel 726. The cursor can be moved on the monitor 719 through a joystick 726a on the operating panel 726 and the operation of this joystick 726a is sensed by the control circuit 725.

Figure 26A:
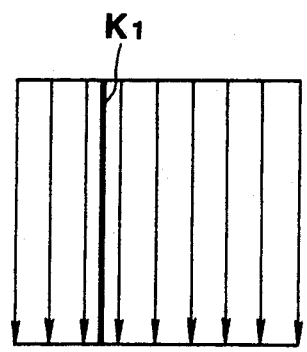
FIGS. 26(A) and 26(B) ar explanatory views showing displayed images by a monitor.
Figure 26B:
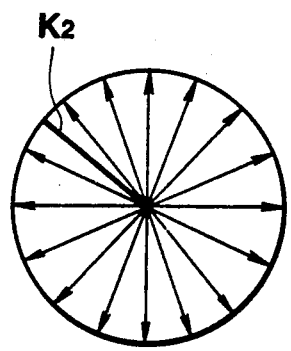

FIG. 26 shows displayed images on the monitor 719 at the time of respective scannings. FIG. 26(A) is of the linear scanning and FIG. 26(B) is of the radial scanning. $K_1$ and $K_2$ represent respective cursors.

The operation of the thus formed embodiment shall be explained. When a linear scanning is first selected through the switching switch on the operating panel 726, the ultrasonic vibrator 702 will be advanced and retreated within the insertable part 701 by the driving force of the motor 708 and, at the same time, a driving signal will be output to the ultrasonic vibrator 702 from the pulser circuit 712 by a signal output from the encoder 709 and the ultrasonic vibrator 702 will be excited to radiate ultrasonic waves. An echo signal reflected by radiating an object to be inspected is received again by the ultrasonic vibrator 702 and is displayed on the monitor 719 through the signal receiving circuit 713, A/D converter 714, memories 715 and 716, switch 717 and D/A converter 718. By repeating such operations, such linearly scanned image as is shown in FIG. 26(A) is obtained.

Then, in order to obtain radially scanning lines of any part of the linearly scanned image, first the joystick 726a on the operating panel 726 is operated to move the cursor $K_1$ to the required part. When the scanning system is switched from the linear scanning to the radial scanning by the switching switch, the linear image displayed on the monitor 719 will be written into the memory 715 and the position of the cursor $K_1$ will be written into the cursor position memorizing circuit 722. The ultrasonic vibrator 702 is advanced and retreated by the motor controlling circuit 723 and motor 708 and is moved to the position designated by the cursor $K_1$ by comparing the signal from the encoder 709 and encoder signal processing circuit 702 with the value written into the cursor position memorizing circuit 722 by the comparing circuit 721.

Then, the radial scanning is made by exciting the ultrasonic vibrator 702 while rotating it and the radially scanned image is displayed on the monitor 719 through the memory 716. In such case, the linearly scanned surface stored in the memory 715 may be displayed like the cursor $K_2$ shown in FIG. 26(B). The radially scanned image displayed on the monitor 719 and the linearly scanned image stored in the memory 715 are displayed as switched by another switch on the operating panel 726 so that the respective position relations may be recognized. The scanning position of the radially scanned image can be moved by the switch on the operating panel 726. In such case, the value stored in the cursor position memorizing circuit 722 will be also changed. Therefore, in case the display is switched to the linearly scanned image stored in the memory 715, the cursor $K_1$ will be displayed in the position corresponding to the scanning position cf the radially scanned image. It is needless to say that, when the linearly scanned image is kept displayed and the cursor $K_1$ is moved, the scanning position of the radially scanned image will be able to be changed.

The change from the linear scanning to the radial scanning is as mentioned above. It is needless to say that, in the case of the change from the radial scanning to the linear scanning, the same operation as is mentioned above may be also made. In such case, the radially scanned image will be stored in the memory 716 and the linearly scanned image will be displayed on the monitor 719 through the memory 715.

As in the above, according to this embodiment, when the scanning positions of the linearly scanned image and radially scanned image are designated by the cursor and the scanning surface is moved, the desired parts of both will be able to be easily observed as related with each other and the position relations of both will be able to be easily recognized.

Also, the linear scanning image and radial scanning image may be displayed in respectively separate monitors.

Figure 27A:
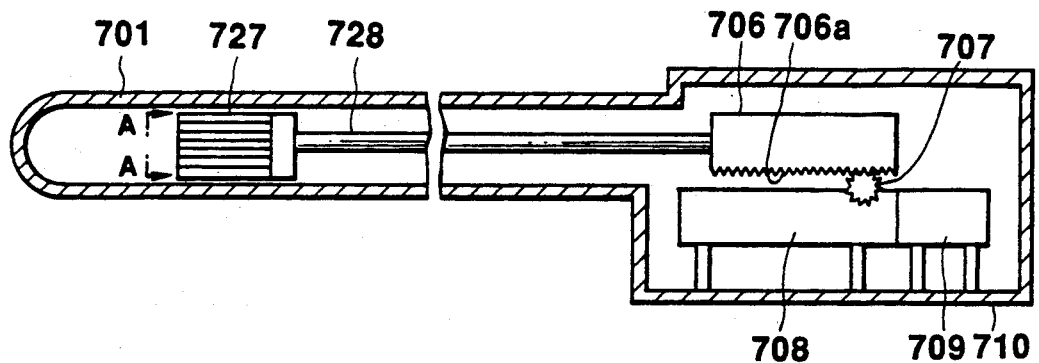
FIG. 27(A) is a sectioned view showing the formation of an ultrasonic observing apparatus driving system.
Figure 27B:
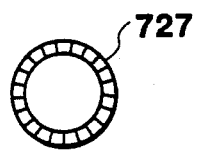
FIG. 27(B) is an elevation in the direction A—A of FIG. 27(A).
Figure 28:
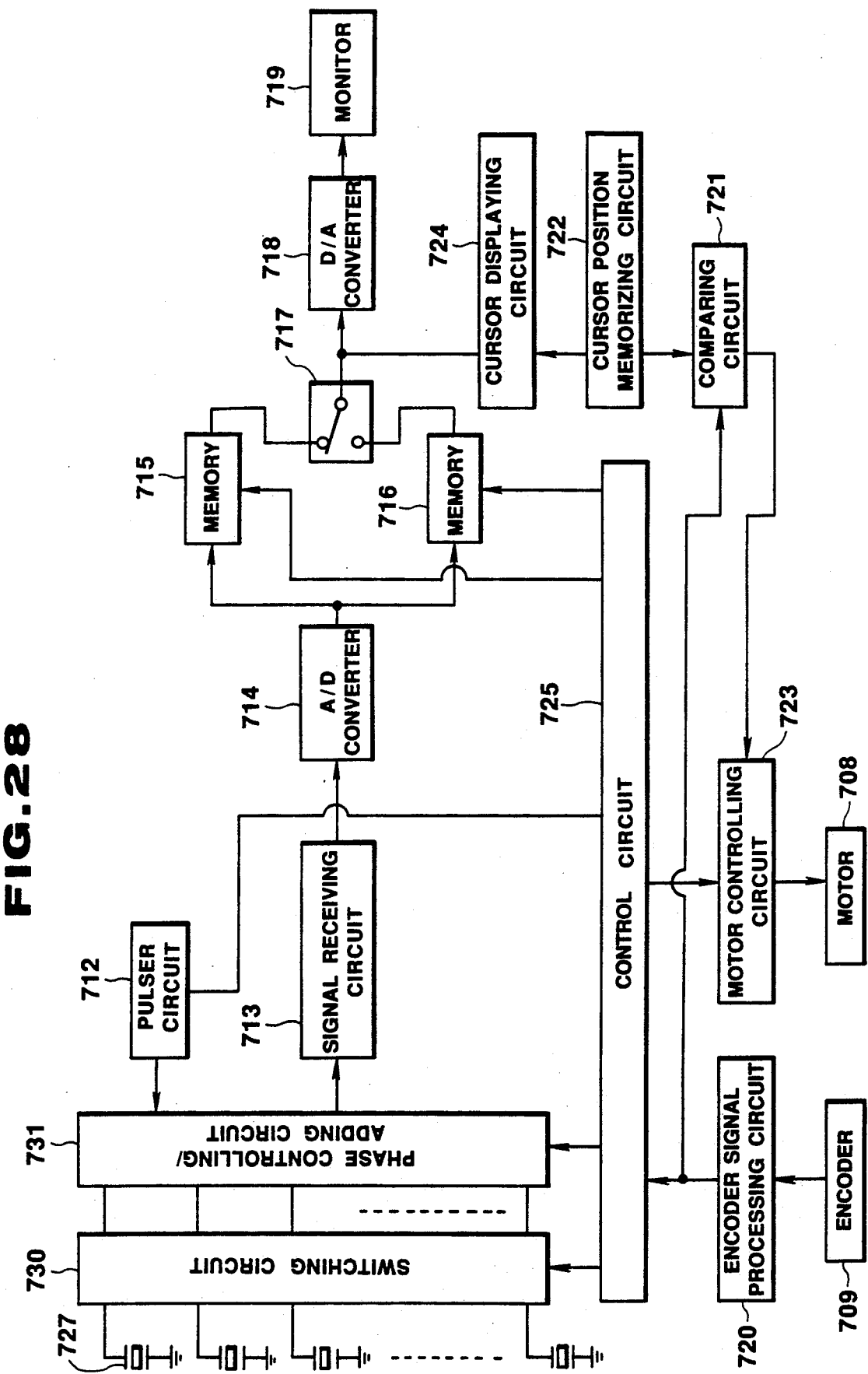

In FIGS. 27 and 28 is shown the tenth embodiment of the present invention.

FIG. 27 is a sectioned view of an essential part relating to this embodiment. The same reference numerals are attached to the parts corresponding to the same parts in the ninth embodiment (also in the embodiments hereinafter). In this embodiment, as shown in FIG. 27(B), an ultrasonic vibrator 727 is formed of many annularly arranged ultrasonic vibrators and is provided at the tip of a shaft 728. A rack 706a is formed on a supporter 706 at the rear end of the shaft 728 and is meshed with a pinion 707 so as to be able to advance and retreat the ultrasonic vibrator 727 the same as in the ninth embodiment.

FIG. 28 is a block diagram of the whole of this embodiment. The annularly arranged ultrasonic vibrators 727 are connected to a switching circuit 730 respectively through signal lines so that any one or group of more of them may be selected. If the ultrasonic vibrators 727 are sequentially switched and excited, a scanning will be electronically possible in the radial direction. The ultrasonic vibrators 727 selected by the switching circuit 730 are connected to a pulser circuit 712 through a phase controlling/adding circuit 731 and are connected to a signal receiving circuit 713. A driving signal from the pulser circuit 712 is given a proper phase difference by the phase controlling/adding circuit 731 and is applied to the respective ultrasonic vibrators 727 and ultrasonic beams emitted to an object to be inspected are focused and scanned. Therefore, the radially scanning motor 704 and encoder 705 in the ninth embodiment are eliminated.

On the other hand, the received signal received by the respective ultrasonic vibrators 727 are given a proper phase difference by the phase controlling/adding circuit 731, are then added and are input into the signal receiving circuit 731. The other formations are substantially the same as in the ninth embodiment. However, the encoder signal processing circuit 720 is connected to only the encoder 709 and the motor controlling circuit 723 is connected to only the motor 708.

In this embodiment, as it is thus formed, when the respective ultrasonic vibrators 727 are switched and selected by the switching circuit 730, a radial scanning will be able to be made. Also, while advancing and retreating the ultrasonic vibrators 727 through the motor 708, pinion 707 and rack 706a, a linear scanning can be made. It is the same as in the ninth embodiment that the ultrasonic vibrators 727 are moved to the position corresponding to any part in a linearly scanned image by driving the motor 708. Thus the radial scanning can be made in the position to which the ultrasonic vibrators are moved. On the contrary, in order to linearly scan any part in a radially scanned image, the ultrasonic vibrators in the position designated by the cursor may be selected by the switching circuit 730 and the motor 708 may be driven.

The other operations and effects are the same as in the ninth embodiment.

Figure 29A:
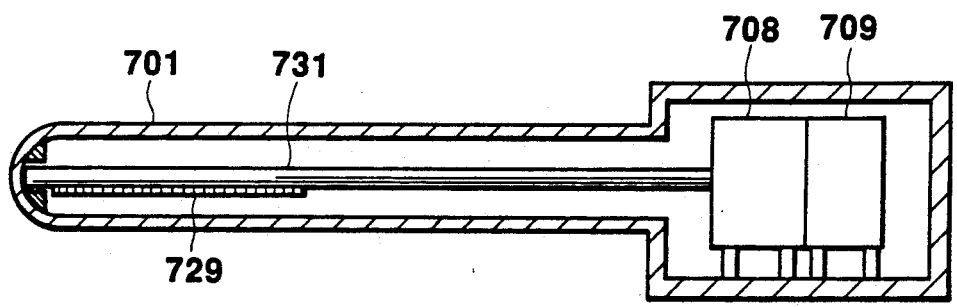
FIGS. 29(A)–29(B) relate to the 11th embodiment of the present invention.
Figure 29B:

FIG. 29 shows the 11th embodiment of the present invention. In this embodiment, the respective ultrasonic vibrators 729 are arranged in a straight line and are excited as sequentially switched by the switching circuit 730 to make a linear scanning. In order to make a radial scanning, the cursor may be moved to any part in a linearly scanned image, the ultrasonic vibrators 729 corresponding to this part may be selected by the switching circuit 730 and the shaft 731 ma be rotated by the motor 708 to integrally rotate the ultrasonic vibrators 729. Also, in order to linearly scan any part in a radially scanned image, the motor 708 may be driven to change the position of the ultrasonic vibrators 729. FIG. 29(B) is a view as seen from the front of the ultrasonic vibrator 729 of this embodiment.

The other formations, operations and effects are the same as in the tenth embodiment. That is to say, the respective scanning positions of the linear scanning and radial scanning can be freely selected to display a tomographic image.

Figure 30:
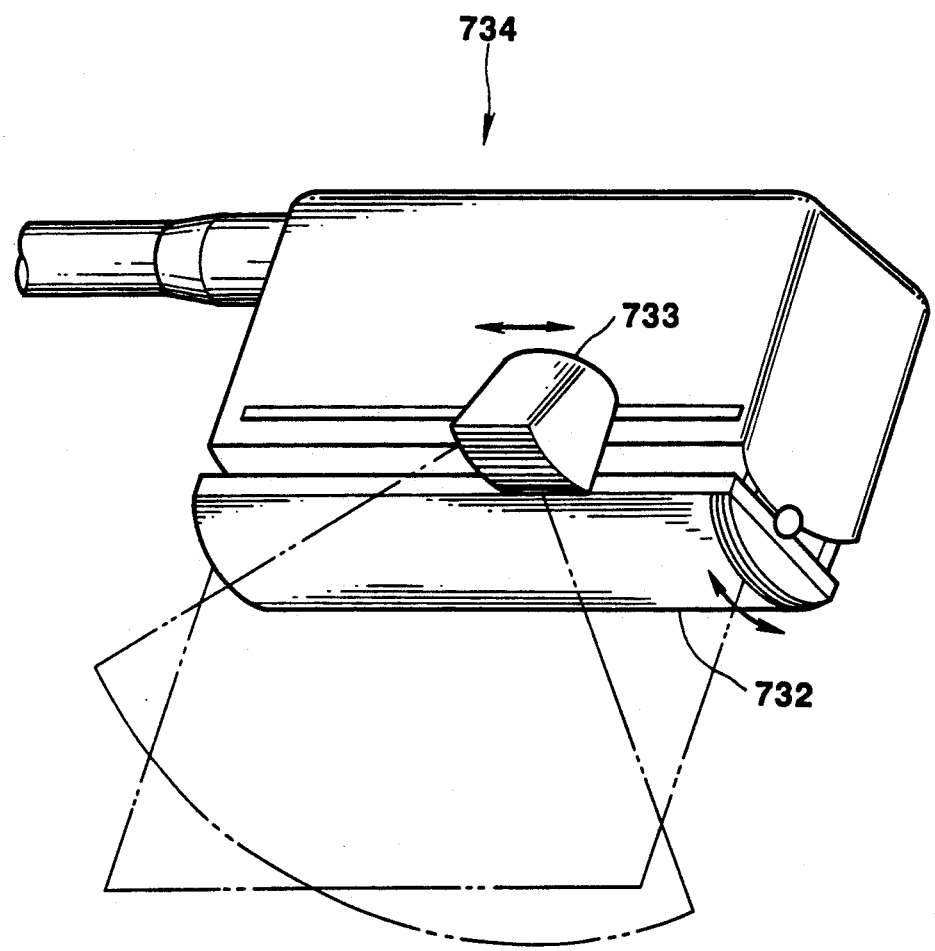
Figure 32A:
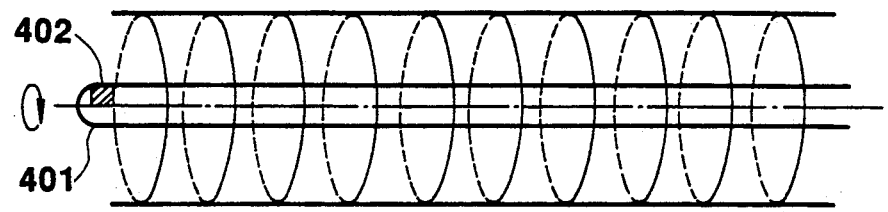
FIGS. 32(A) to 32(C) and FIGS. 33(A) and 33(B) are explanatory views showing conventional scanning systems for obtaining radial images and linear images.
Figures 32B, 32C:
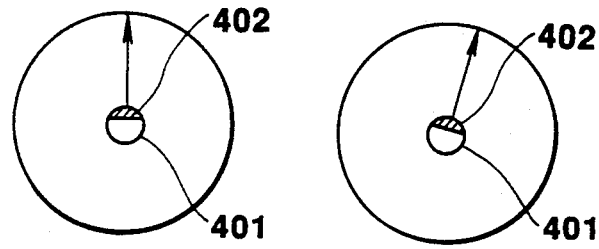
Figure 33A:
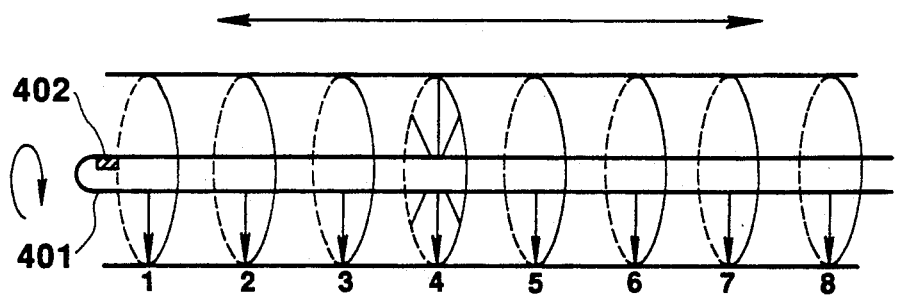
Figure 33B:
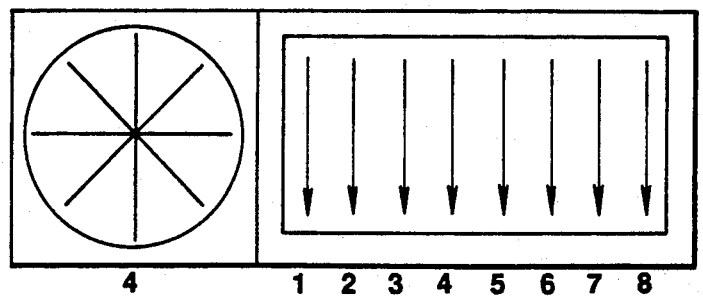
Figure 34A:
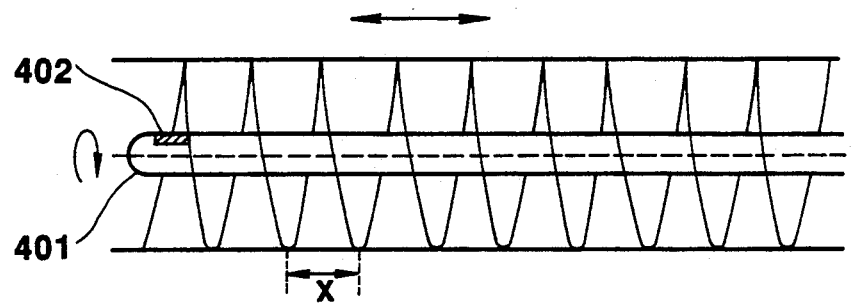
FIGS. 34(A) to 34(C) are explanatory views showing spiral scanning systems for obtaining radial images and linear images.
Figure 34B:
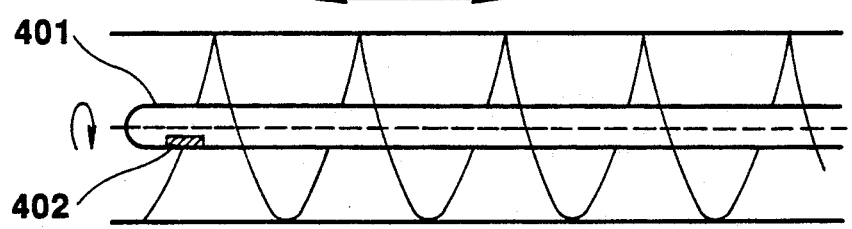
Figure 34C:
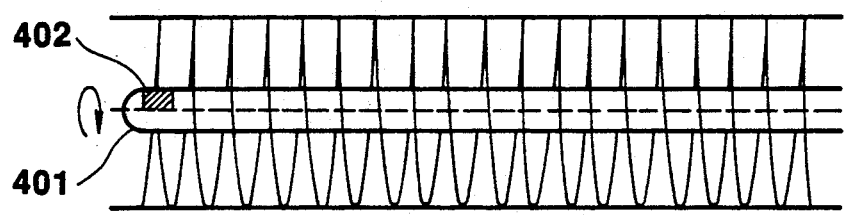

In FIGS. 30 and 31 is shown the 12th embodiment of the present invention.

In this embodiment, as shown in FIG. 30, a probe 734 is provided with two independent ultrasonic vibrators of a linear electronic scanning ultrasonic vibrator 732 and a sector or convex electronic scanning ultrasonic vibrator 733 and the respective vibrators 732 and 733 are made movable by motors 741 and 743 in the direction intersecting at right angles with the scanning surfaces of the respective vibrators.

As shown in FIG. 31, for the respective vibrators 732 and 733 are provided respectively switch circuits 730, position controlling/adding circuits 731, pulser circuits 712, signal receiving circuits 713, A/D converters 714 and memories 715 and 716. Also, motors 741 and 743 are connected to a motor controlling circuit 723. Encoders 742 and 744 respectively sensing the rotation amounts of the motors 741 and 743 are connected to an encoder signal processing circuit 720.

The other formations, operations and effects are the same as in the tenth embodiment. That is to say, by operating the motors 741 and 743, the respective scanning positions of the linear scanning and sector or convex scanning may be freely selected to display a tomographic image.

As in the above, according to the 9th to 12th embodiments, a cursor can be displayed in a required part in a tomographic image scanned by one scanning system, further a scanning surface by another scanning system can be moved to that part and therefore both tomographic images can be displayed as related with each other. Also, the position relations of both tomographic images can be positively caught. Therefore, the diagnosis by ultrasonic waves can be effectively made.

It is apparent that, in this invention, different working modes can be formed on the basis of this invention without deviating from the spirit and scope of the invention. This invention is not restricted by its specific working mode except being limited by the appended claims.

What is claimed is:

1. An ultrasonic observing apparatus comprising:
   an ultrasonic wave transmitting and receiving means, provided inside a tip of a probe, for transmitting and receiving ultrasonic waves;
   a first scanning means for rotating said ultrasonic wave transmitting and receiving means to move a direction inside said probe in which said ultrasonic wave transmitting and receiving means transmits and receives waves so that a first ultrasonic tomographic image may be obtained;
   a second scanning means for advancing and retreating said ultrasonic wave transmitting and receiving means to move a direction inside said probe in which said ultrasonic wave transmitting and receiving means transmits and receives waves so that a second ultrasonic tomographic image intersecting with said first ultrasonic tomographic image may be obtained; and
   a control means for controlling said first scanning means and said second scanning means as related with each other wherein said ultrasonic wave transmitting and receiving means is spirally moved inside said probe by said first and second scanning means.

2. An ultrasonic observing apparatus according to claim 1 wherein said control means includes a means for simultaneously operating said first scanning means and said second scanning means as synchronized with each other.

3. An ultrasonic observing apparatus according to claim 1 wherein said control means includes an operating means for simultaneously operating said first scanning means and said scanning means, a designating means for designating at least one of a position of a scanning surface of said first scanning means for obtaining said first ultrasonic tomographic image and the position of the scanning surface of said second scanning means for obtaining said second ultrasonic tomographic image within respective scanning ranges of said first scanning means and said second scanning means and an extracting means for extracting only a signal corresponding to the position designated by said designating means among signals obtained by receiving waves by said ultrasonic wave transmitting and receiving means.

4. An ultrasonic observing apparatus according to claim 1 which further comprises a displaying means for displaying said first ultrasonic tomographic image and said second ultrasonic tomographic image based on signals obtained by receiving waves by said ultrasonic wave transmitting and receiving means and wherein said control means includes a designating means for designating a position of a scanning surface of the other scanning means on the tomographic image of one displayed by said displaying means when operating one scanning means of said first scanning means and said second scanning means and a means for moving the scanning surface of said other scanning means to the position designated by said designating means.

5. An ultrasonic probe comprising:
   an ultrasonic wave transmitting and receiving part for transmitting and receiving ultrasonic waves;
   a first driving means for rotating said ultrasonic wave transmitting and receiving part;
   a second driving means for advancing and retreating said ultrasonic wave transmitting and receiving part; and
   a control means for simultaneously operating said first driving means and said second driving means as synchronized with each other.

6. An ultrasonic probe according to claim 5 wherein, said control means having a means for variably controlling a speed of said rotary motion and a speed of said advancing and retreating motion by keeping a ratio of the speeds of first and second driving means constant.

7. An ultrasonic probe according to claim 5 wherein said ultrasonic wave transmitting and receiving part includes an ultrasonic vibrator capable of rotating, advancing and retreating.

8. An ultrasonic probe according to claim 5 wherein said control means includes a means for giving said first driving means and second driving means a common driving signal for operating both driving means as synchronized.

9. An ultrasonic probe according to claim 5 wherein said control means includes a means for giving a driving signal for operating the driving means to one of said first driving means and said second driving means and a means for detecting an operating position of said one driving means and giving a driving signal corresponding to said position to the other driving means.

10. An ultrasonic probe according to claim 5 wherein said control means includes a means for giving one of said first driving means and said second driving means a driving signal for operating said driving means and a means for dividing a frequency of said driving signal given to said one driving means and giving said divided frequency signal to the other driving means.

11. An ultrasonic probe according to claim 5 further comprising a means for generating ultrasonic pulses synchronized with the operation of said first driving means and said second driving means by said control means and transmitted from said ultrasonic wave transmitting and receiving part.

12. An ultrasonic observing apparatus comprising:
    an ultrasonic wave transmitting and receiving part for transmitting and receiving ultrasonic waves;
    a driving means for simultaneously advancing, retreating and rotating said ultrasonic wave transmitting and receiving part;
    a designating means for designating a position of a scanning surface for obtaining an ultrasonic tomographic image; and
    an extracting means for extracting only a signal corresponding to the position designated by said designating means among signals obtained by receiving waves by said ultrasonic wave transmitting and receiving part.

13. An ultrasonic observing apparatus according to claim 12 wherein said ultrasonic wave transmitting and receiving part includes an ultrasonic vibrator capable of rotating, advancing and retreating.

14. An ultrasonic observing apparatus according to claim 12 further comprising a displaying means for displaying an ultrasonic tomographic image formed by a signal extracted by said extracting means.

15. An ultrasonic observing apparatus according to claim 12 wherein said designating means includes a sensing means operatively connected to said driving means and sensing a specific operating position of said driving means and a means for changing position of said sensing means.

16. An ultrasonic observing apparatus according to claim 12 wherein said designating means includes a detecting means for detecting a signal corresponding to an operating position of said driving means and a designating means for designating a specific timing among signals detected by said detecting means.

17. An ultrasonic observing apparatus comprising:
an ultrasonic wave transmitting and receiving means for transmitting and receiving ultrasonic waves;
a first scanning means for rotating said ultrasonic wave transmitting and receiving means;
a second scanning means for advancing and retreating said ultrasonic wave transmitting and receiving means;
a displaying means for displaying a first ultrasonic wave cross-sectioned layer image obtained by rotating said ultrasonic wave transmitting and receiving means by said first scanning means and a second ultrasonic wave cross-sectioned layer image obtained by advancing and retreating and ultrasonic wave transmitting and receiving means by said second scanning means;
a position designating means for freely designating a position of a scanning surface of the other scanning means on the ultrasonic wave cross-sectioned layer image of one displayed by said displaying means when operating one scanning means of said first scanning means and said second scanning means; and
a means for moving the scanning surface of said other scanning means to the position designated by said position designating means.

18. An ultrasonic observing apparatus according to claim 17 wherein said first scanning means makes a linear scanning and said second scanning means makes a radial scanning.

19. An ultrasonic observing apparatus according to claim 18 wherein said ultrasonic wave transmitting and receiving means includes an ultrasonic vibrator, said first scanning means includes a first driving means for advancing and retreating said ultrasonic vibrator and said second scanning means includes a second driving means for rotating said ultrasonic vibrator.

20. An ultrasonic observing apparatus according to claim 19 wherein said moving means operates said first driving means or second driving means to move said scanning surface.

21. An ultrasonic observing apparatus according to claim 18 wherein said ultrasonic wave transmitting and receiving means includes a plurality of annularly arranged ultrasonic vibrators, said first scanning means includes a driving means for advancing and retreating said ultrasonic vibrators and said second scanning means includes a means for selectively exciting at least one of said plurality of ultrasonic vibrators.

22. An ultrasonic observing apparatus according to claim 21 wherein said moving means changes the vibrator to be excited among said plurality of ultrasonic vibrators when moving a scanning surface of said first scanning means and operates said driving means moving the scanning surface of said second scanning means.

23. An ultrasonic observing apparatus according to claim 18 wherein said ultrasonic wave transmitting and receiving means includes a plurality of linearly arranged ultrasonic vibrators, said first scanning means includes a means for selectively exciting at least one of said plurality of ultrasonic vibrators and said second scanning means includes a driving means for rotating said ultrasonic vibrators.

24. An ultrasonic observing apparatus according to claim 23 wherein said moving means operates said driving means when moving a scanning surface of said first scanning means and changes the vibrator to be excited among said plurality of ultrasonic vibrators when moving the scanning surface of said second scanning means.

25. An ultrasonic observing apparatus according to claim 17 wherein said ultrasonic wave transmitting and receiving means includes a first vibrator group and second vibrator group respectively include a plurality of ultrasonic vibrators, said first scanning means includes a means for selectively exciting at least one ultrasonic vibrator in said first vibrator group, said second scanning means includes a means for selectively exciting at least on ultrasonic vibrator in said second vibrator group and said moving means includes a means for changing respective positions of said first vibrator group and said second vibrator group.

26. An ultrasonic observing apparatus according to claim 17 wherein said designating means includes a means for displaying position of a designated scanning surface on said one tomographic image displayed by said displaying means.

* * * * *